United States Patent
Burdea

(10) Patent No.: US 9,724,598 B2
(45) Date of Patent: Aug. 8, 2017

(54) BIMANUAL INTEGRATIVE VIRTUAL REHABILITATION SYSTEMS AND METHODS

(71) Applicant: Bright Cloud International Corp., Highland Park, NJ (US)

(72) Inventor: Grigore Cristian Burdea, Highland Park, NJ (US)

(73) Assignee: Bright Cloud International Corp., Highland Park, NJ (US)

( * ) Notice: Subject to any disclaimer, the term of this patent is extended or adjusted under 35 U.S.C. 154(b) by 589 days.

(21) Appl. No.: 14/032,360

(22) Filed: Sep. 20, 2013

(65) Prior Publication Data

US 2014/0121018 A1 May 1, 2014

Related U.S. Application Data

(60) Provisional application No. 61/704,165, filed on Sep. 21, 2012, provisional application No. 61/869,857, filed on Aug. 26, 2013.

(51) Int. Cl.
*A63F 13/20* (2014.01)
*G06F 19/00* (2011.01)
*A63F 13/211* (2014.01)

(52) U.S. Cl.
CPC ............ *A63F 13/06* (2013.01); *A63F 13/211* (2014.09); *G06F 19/3481* (2013.01)

(58) Field of Classification Search
CPC .................................................. G06F 19/3481
USPC ...................... 463/1–6, 35, 37, 40–42; 482/4
See application file for complete search history.

(56) References Cited

U.S. PATENT DOCUMENTS

| 6,334,778 B1* | 1/2002 | Brown | A61B 5/6896 273/429 |
| 2008/0281633 A1* | 11/2008 | Burdea | A61B 5/0002 705/2 |
| 2012/0157263 A1* | 6/2012 | Sivak | A61H 1/0285 482/4 |

OTHER PUBLICATIONS

"Optimising Engagement for Stroke Rehabilitation Using Serious Games" by Burke et al, 2009.*
"Intensive nutritional supplements can improve outcomes in stroke rehabilitation" by Rabadi et al 2008.*

(Continued)

*Primary Examiner* — David L Lewis
*Assistant Examiner* — Ross Williams
(74) *Attorney, Agent, or Firm* — Chiesa Shahinian & Giantomasi PC

(57) ABSTRACT

Virtual rehabilitation serious games have gained increasing clinical acceptance in the therapy of large patient populations (stroke and traumatic brain injury). This is due to their ability to motivate the patient, as well as intrinsic large number of movement repetitions they generate. These repetitions are key to inducing brain plasticity and facilitating patient recovery. Unfortunately, bi-manual therapy, while potentially more efficacious, is less developed at this time. We present a novel system and method, for bi-manual game-based integrative therapy that combines physical and cognitive training in integrative game play sessions. It is built around the new Razer Hydra Game interface that track's the patient's arms in 3D and detects trigger pressing. A series of custom games designed to improve focusing, decision making (executive function), short term and long term memory, are played with progressive difficulty.

20 Claims, 18 Drawing Sheets

(56) References Cited

OTHER PUBLICATIONS

Cameirão MS, Bermúdez I Badia S, Duarte Oller E, Verschure PF. The rehabilitation gaming system: a review. Stud Health Technol Inform. 2009;145:65-83. Review. PubMed PMID: 19592787.*

Liu, Huajun, et al. "Realtime human motion control with a small number of inertial sensors." Symposium on Interactive 3D Graphics and Games. ACM, 2011.*

Wu, CY. et al., "Randomized trial of distributed constraint-induced therapy versus bilateral arm training for the rehabilitation of upper-limb motor control and function after stroke." Neurorehabil Neural Repair. 2011, vol. 25(2), pp. 130-139.

Burdea, GC. "Virtual rehabilitation—benefits and challenges." Methods Inf Med. 2003; vol. 42(5), pp. 519-523.

Brooks, CA. et al., "Traumatic brain injury: designing and implementing a population-based follow-up system." Arch Phys Med. Rehabil. 1997; vol. 78(8), pp. 26-30.

Lin, KC. et al., "The effects of bilateral arm training on motor control and functional performance in chronic stroke: a randomized controlled study." Neurorehabil Neural Repair. 2010; vol. 24(1), pp. 42-51.

Optale, G. et al., "Controlling memory impairment in elderly adults using virtual reality memory training: a randomized controlled pilot study." Neurorehabil Neural Repair. 2010; vol. 24(4), pp. 348-357.

Burdea, GC. et al., "The Rutgers Arm II rehabilitation system—a feasibility study." IEEE Trans Neural Sys Rehab Eng, vol. 18(5), pp. 505-514.

Roger, VL. et al., "Executive summary: heart disease and stroke statistics—2012 update: a report from the American Heart Association.", Circulation, 2012; vol. 125(1), pp. 188-197.

Cauraugh, JH. et al., "Bilateral movement training and stroke motor recovery progress: a structured review and meta-analysis." Hum. Mov. Sci., 2010; vol. 29(5), pp. 853-870.

Ausenda, CD. et al., "Transfer of motor skill learning from the healthy hand to the paretic hand in stroke patients: a randomized controlled trial." Eur. J. Rehabil Med., 2011; vol. 47(3), pp. 417-425.

Wang, M. et al., "Neuronal basis of age-related working memory decline." Nature, 2011; vol. 476(7359), pp. 210-213.

Duncan, PW. et al., "Reliability of the Fugl-Meyer assessment of sensorimotor recovery following cerebrovascular accident." Phys Ther. 1983; vol. 63(10), pp. 1606-1610.

Unity Technologies, Reference Manual. San Francisco, CA., 2010.
Sixense Entertainment, Razer Hydra Master Guide, pp. 1-11, 2011.
CNet Leap Motion controller review: Virtual reality for your hands. Jul. 22, 2013. http://www.cnet.com/products/leap-motion-controller/.

* cited by examiner

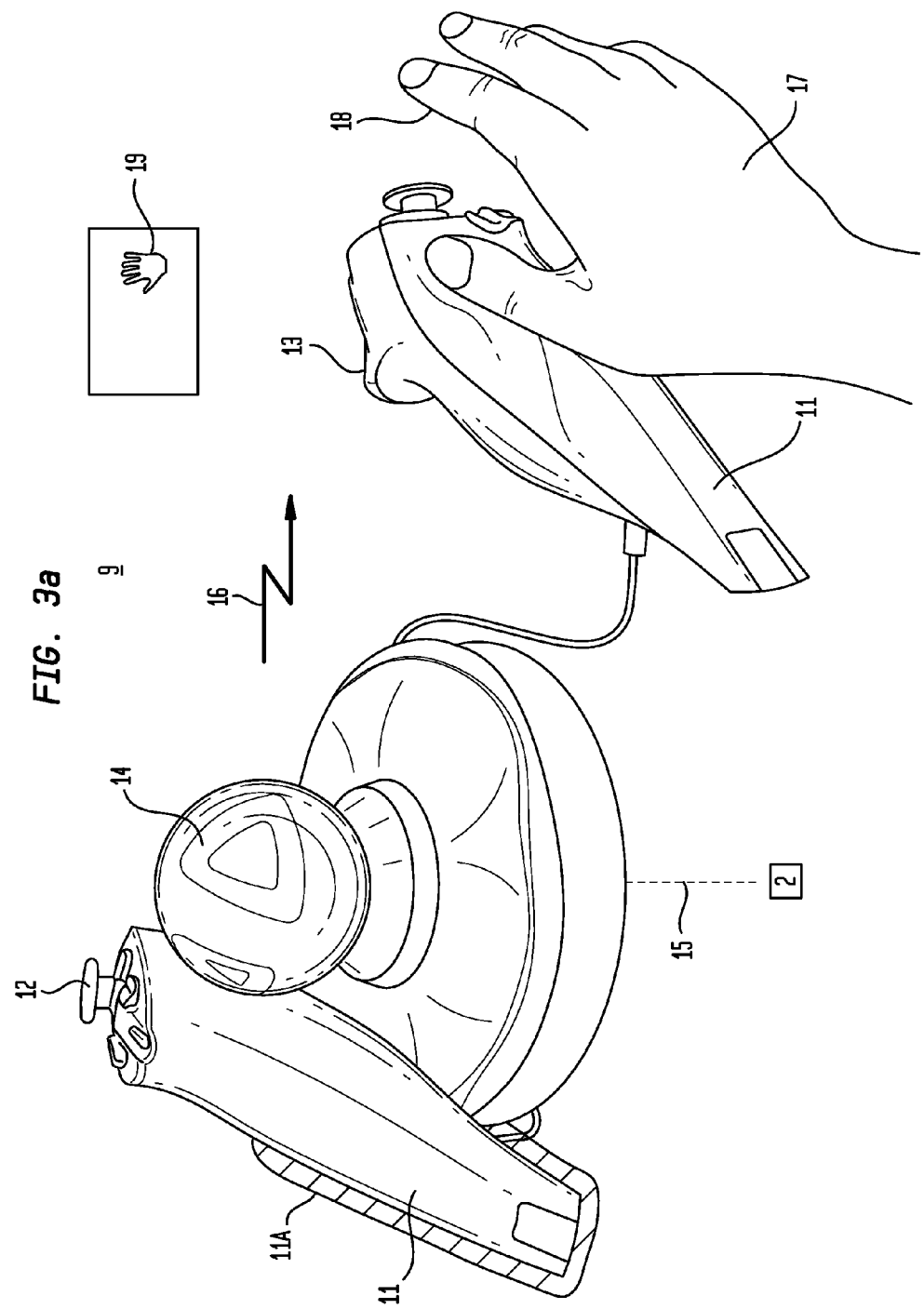

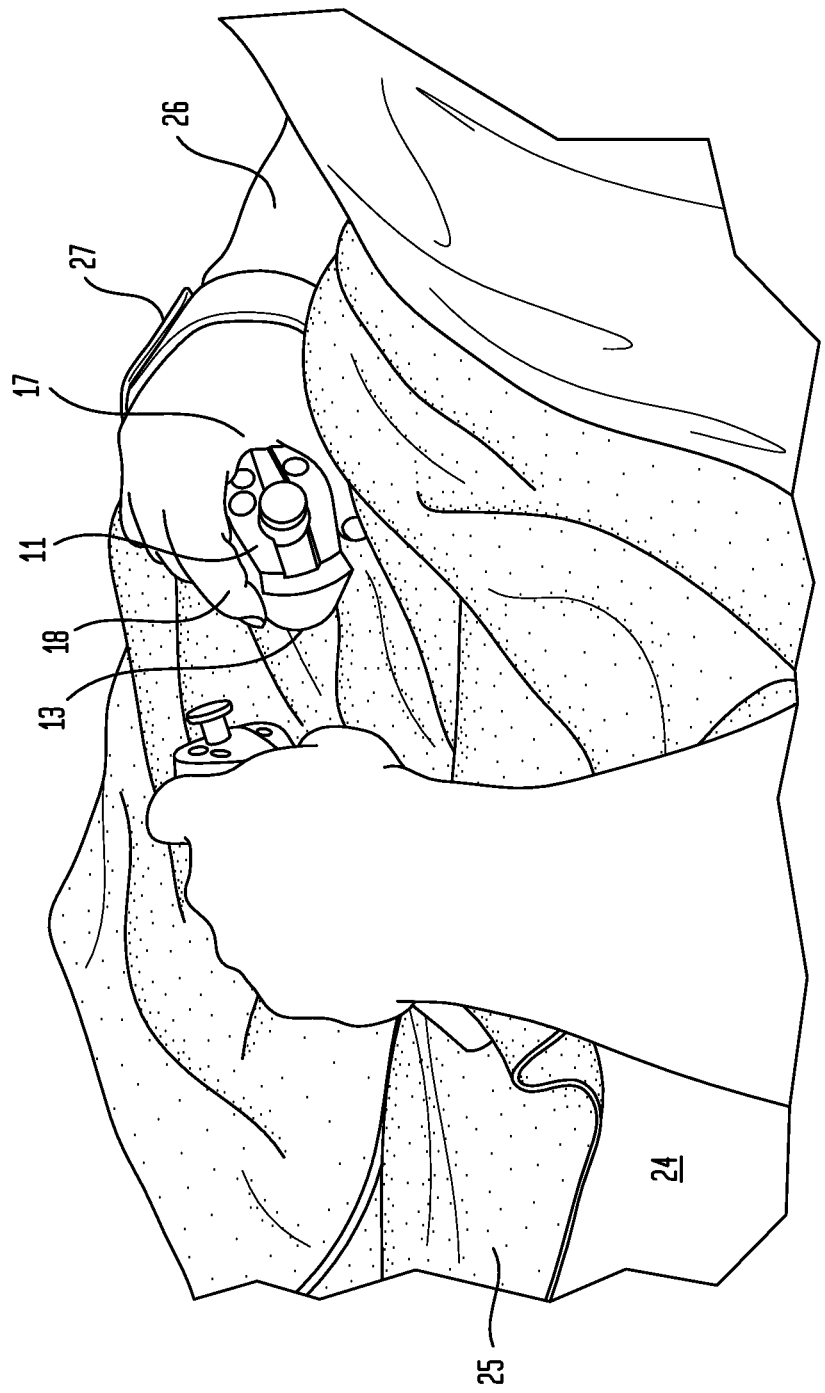

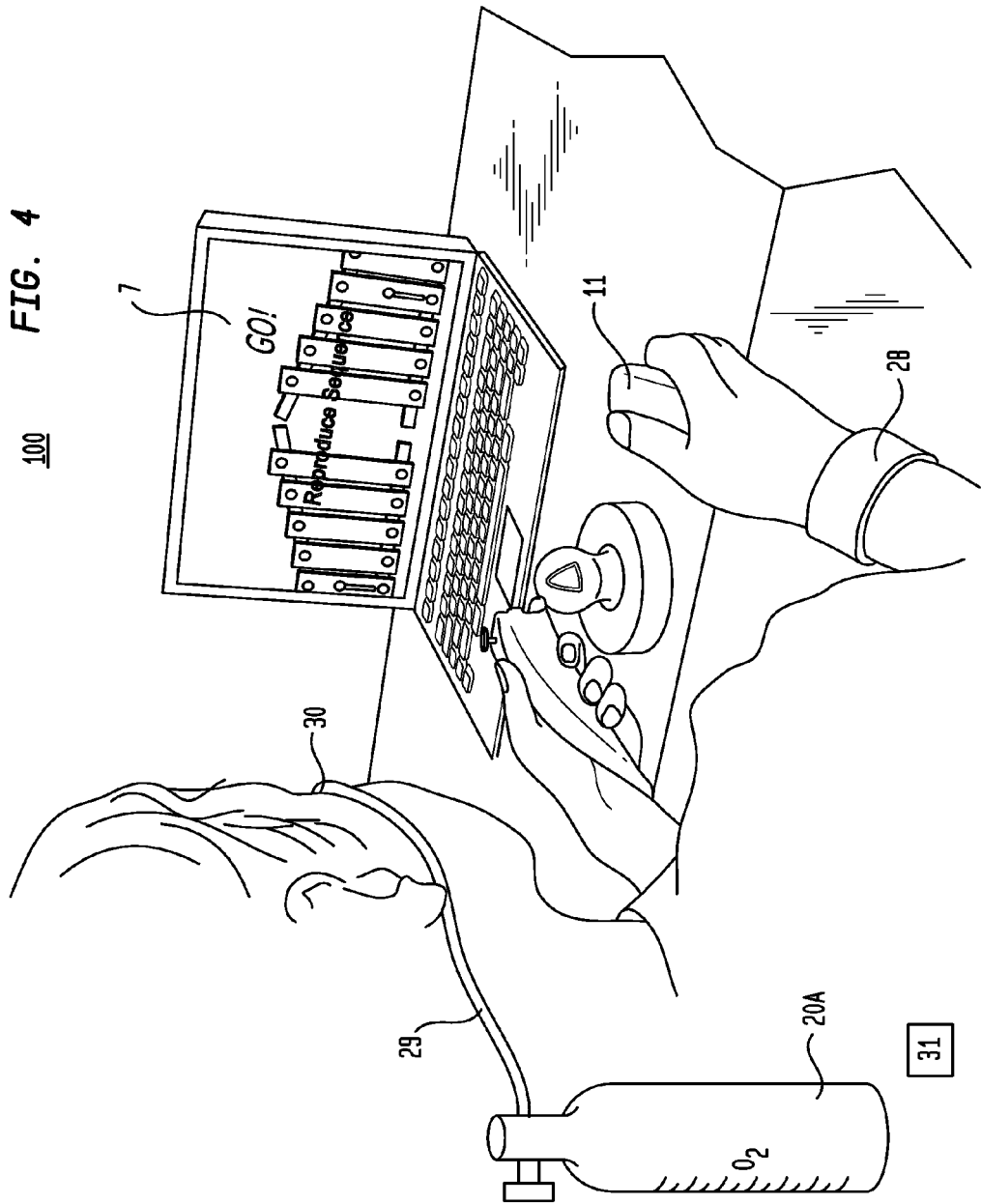

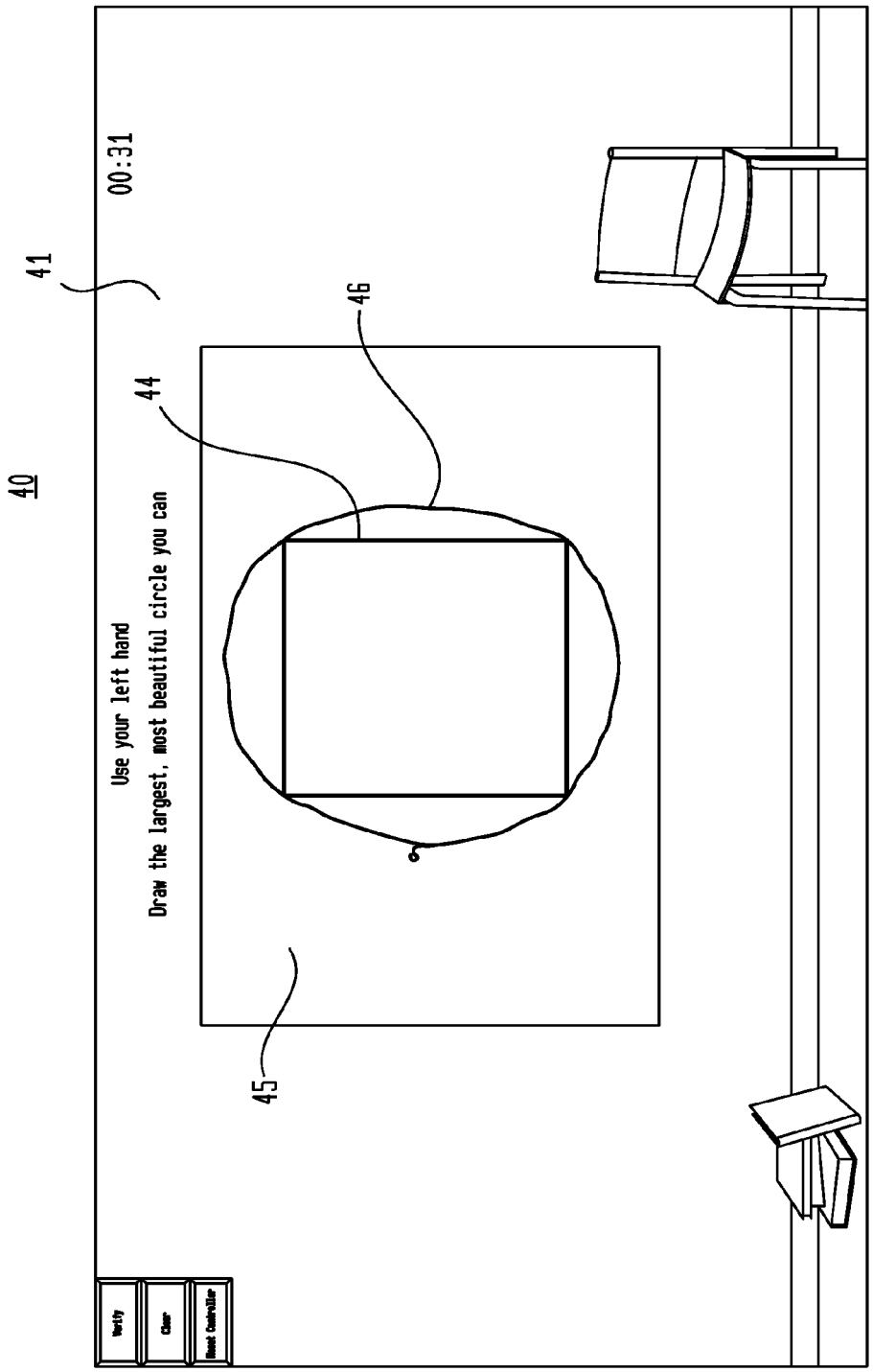

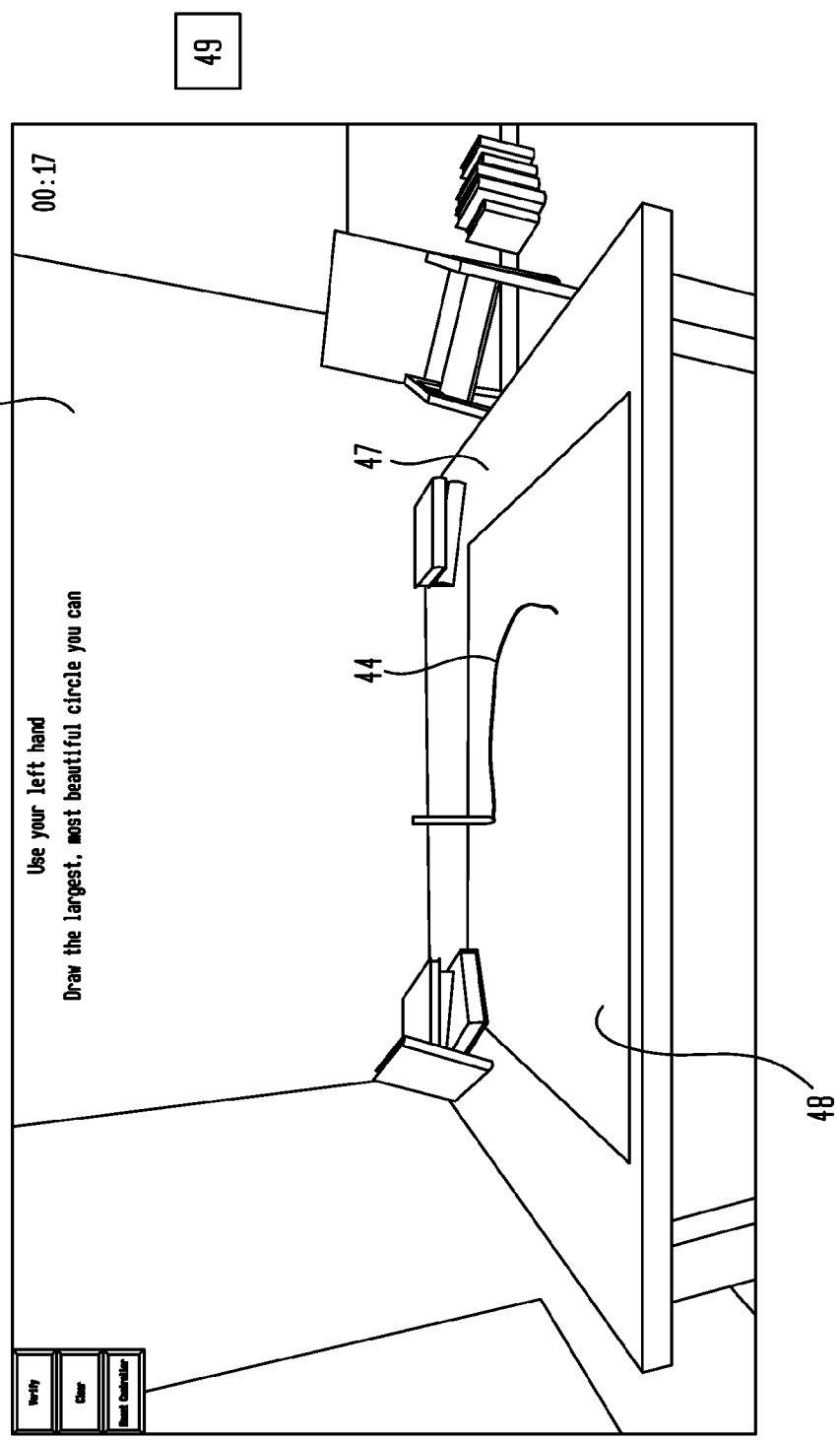

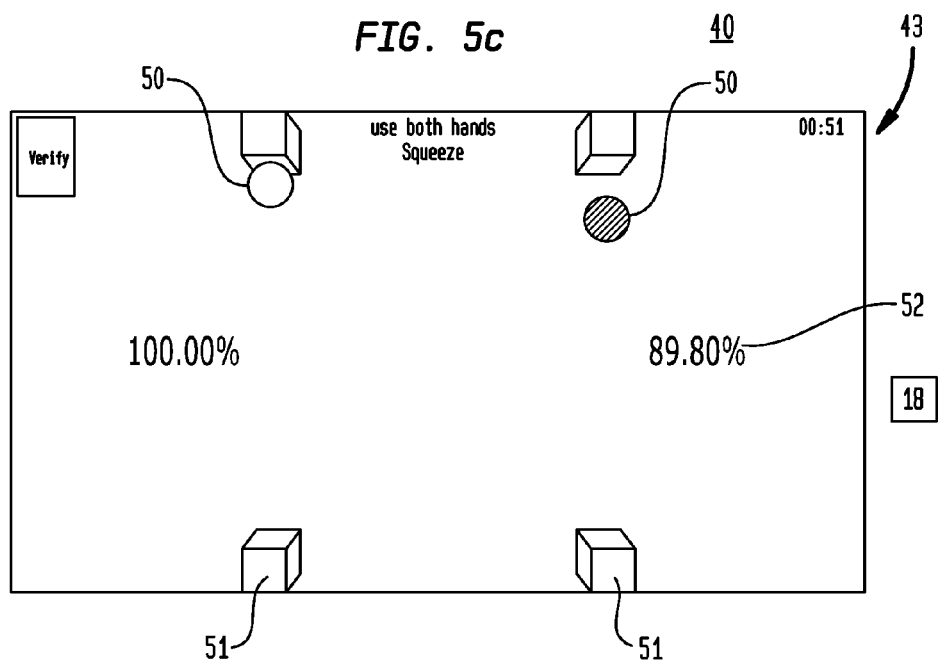
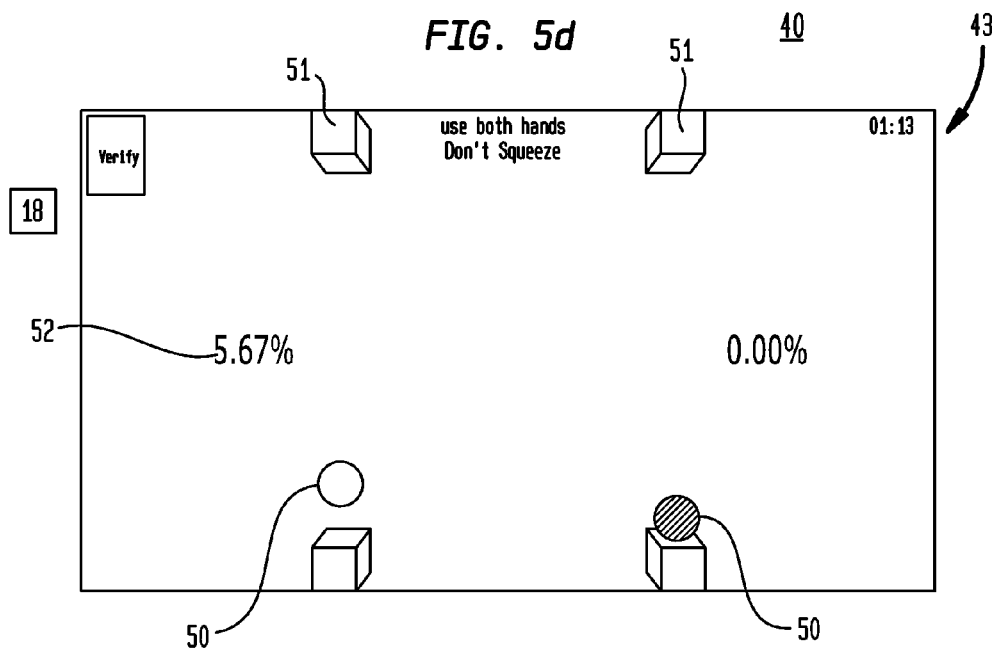

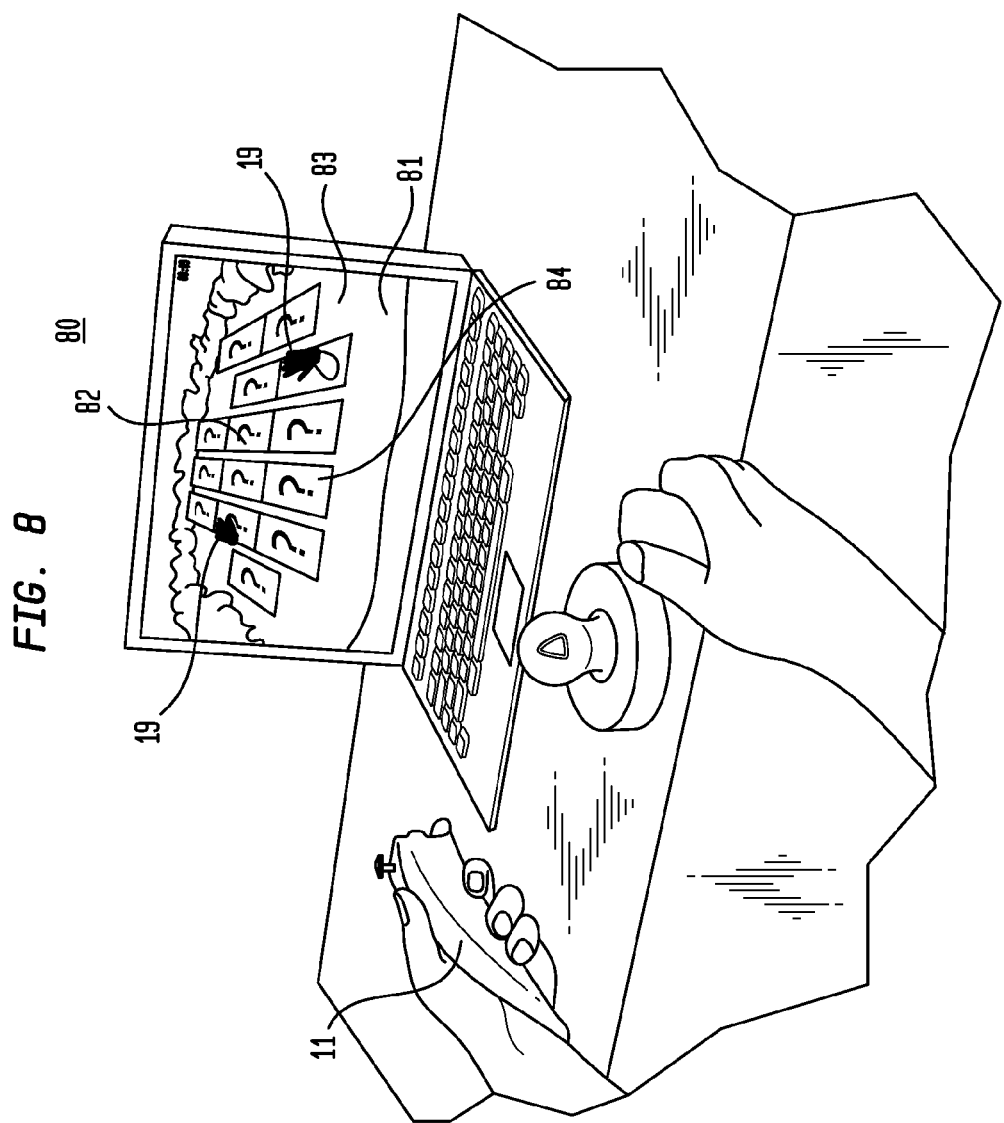

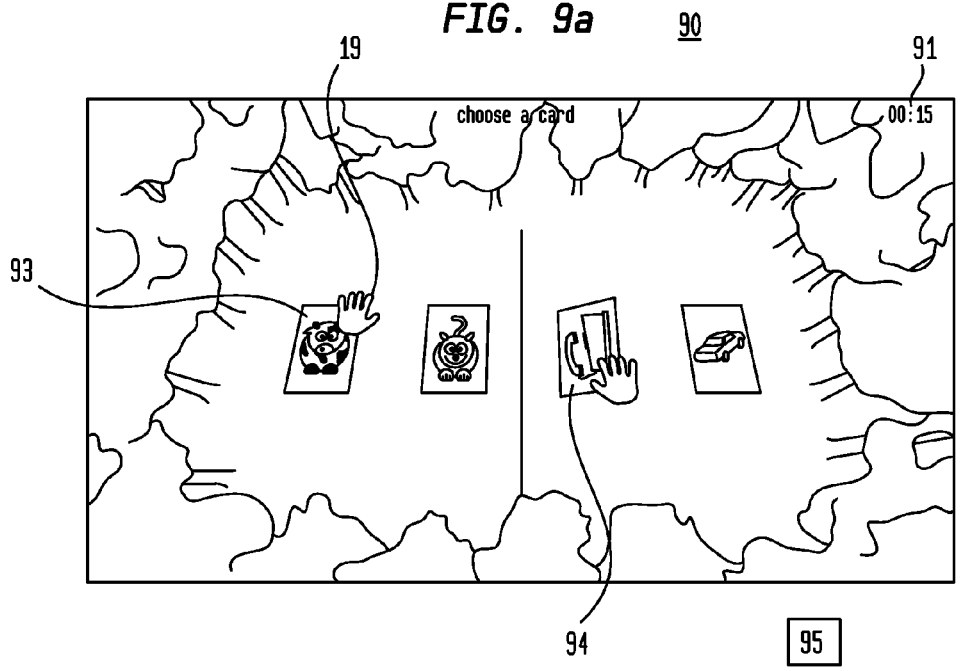
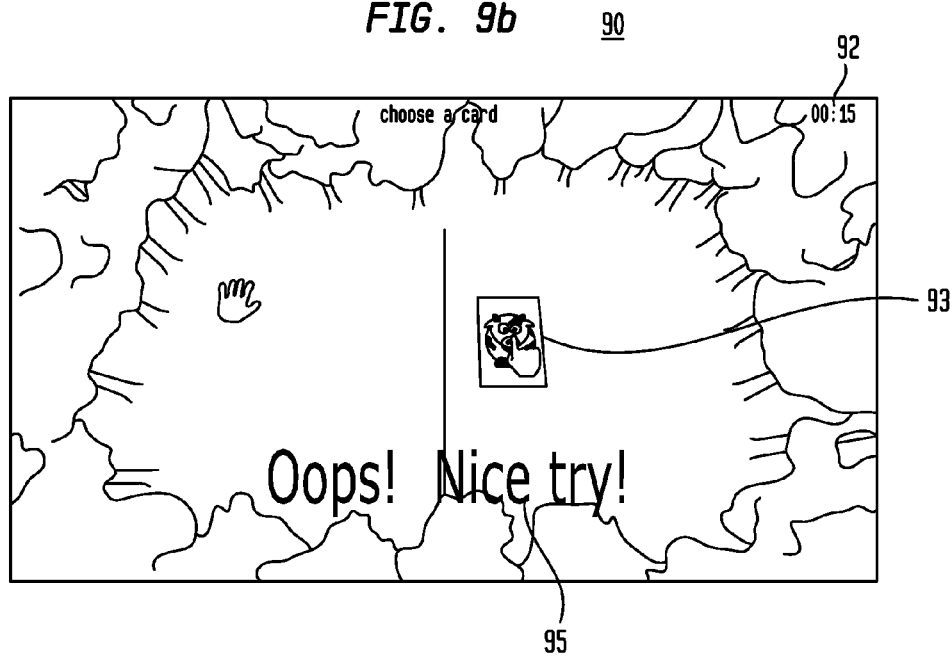

BIMANUAL INTEGRATIVE VIRTUAL REHABILITATION SYSTEMS AND METHODS

CROSS REFERENCE TO RELATED APPLICATIONS

The present application claims the benefit of and priority to U.S. Provisional Patent Application No. 61/704,165, filed on Sep. 21, 2012, and also claims the benefit of and priority to U.S. Provisional Patent Application No. 61/869,857, filed on Aug. 26, 2013, both of which are hereby fully incorporated herein by reference.

BACKGROUND OF THE INVENTION

Stroke is the leading cause of disability in the US, with 795,000 Americans suffering one each year. See Reference No. 1. All references are listed at the end of the specification. Traditional physical rehabilitation of the paretic arm involves passive movement, compensatory training on the less involved arm, electrical stimulation, to which more recently has been added constraint induced therapy to combat learned non-use of the hemiplegic hand. See Reference No. 2. These are uni-manual training approaches involving a single arm which do not take into account the prevalence of activities of daily living (ADLs) which involve both arms.

Another drawback of uni-manual training is diminished neural cross talk to mirror motor areas associated with bimanual activities. A meta analysis of 48 stroke studies to determine the cumulative effect of bilateral arm training on motor capabilities post-stroke (Reference No. 3) did however find a significant effect post training involving bimanual repeated reach movements timed to auditory cues. Another argument in favor of bilateral training is a recent randomized controlled study of stroke patients at the end of their outpatient therapy. See Reference No. 4. Researchers found, for the first time, that training the healthy arm (in a peg-hoard filling task) resulted in a 23% functional improvement the non-trained paretic arm. Researchers also observed improvement in bilateral tasks performance in the experimental group. The control group, which did not train, had no significant difference from baseline. These studies point to the untapped advantages of bimanual training and the present application.

In is known in the art that numerous task-related repetitions are needed to produce changes in the brain. Repetitions, while necessary to induce recovery through brain plasticity, can lead to lack of engagement (attendance to task) by the patient. Second only to the amount of practice, feedback on performance is a key element in motor training and a way to engage the patient. Knowledge of performance feedback can be provided by the therapist (present next to the patient), or through graphics in a virtual rehabilitation setting (Reference No. 5), where the therapist, may be remote. Virtual rehabilitation benefits focus, motivation, and provides intensive training.

Stroke survivors, as well as other patient populations present with both motor and cognitive deficits. See Reference No. 6. Typically their short term and long term memory are affected, as are decision making (executive function), and the ability to focus. Most stroke patients also get depressed. Under the current fractionated care system, such patients are attended by therapists, as well as psychologists or psychiatrists, in separate sessions. This care delivery method is costly and does not exploit fully the body-mind continuum. As opposed to patients who are post-traumatic brain injury and predominantly young, the elderly form the majority of stroke survivors. For them, the situation worsens due to age related cognitive decline. See Reference No. 7. One age related cognitive deficit is diminished ability for split attention (or dual-tasking). These patients need a system designed from the start for integrative cognitive and motor therapy, in order to minimize costs and maximize outcomes. Such system would use therapeutic games that pose both cognitive and whole arm motor demands, and train grasping in dual tasks. The system should automatically adapt to the patient's functioning level, thus making games winnable, so to improve morale (reduce depression). Games, such as cognitive games, mediate many repetitions, so to facilitate improvement or at least maintenance of function over time. Users that benefit most are the elderly with frequent mild cognitive impairment developing into dementia.

There are indications that bimanual training induces higher functional improvements compared to uni-manual training. A recent randomized controlled study (Reference No. 8) was performed on patients chronic post-stroke, half doing bimanual training and the controls doing training of the affected arm, with some coping mechanism (assistance) from the other arm. While both groups had the same training duration and intensity, those doing bimanual training had a 9 points larger improvement in motor function (as measured by their Fugl Meyer Assessment (reference 9) scores) vs. controls. More recently a randomized study of 36 nursing home residents was performed to try to lessen cognitive decline and improve memory function. See Reference 10. The experimental group showed significant improvements in long-term recall and in several other aspects of cognition, while controls showed progressive decline. The above findings motivate the system described here, a bimanual therapy system that simultaneously addresses motor and cognitive impairments of patients post-stroke, post TBI, or those with Mild Cognitive impairments (MCI) developing into dementia. This novel integrative therapy uses custom, adaptable, bimanual virtual reality games, which combine into gradated therapy sessions.

SUMMARY OF THE INVENTION

In accordance with an aspect of the present invention, systems and methods of providing therapy to a patient having a first arm, a first hand, a second arm and a second hand, are provided. In accordance with an aspect of the method, the following steps are performed: a video game is executed on a computer and action from the video game is portrayed on a display, and through sound, the action being viewed and heard by the patient. Then, the patient holds a first component of a game controller in the first hand and manipulates a button on the first component of the game controller with the first hand and moves the first component of the game controller with the first hand and the first arm to control the video game. The patient also holds a second component of a game controller in the second hand and manipulates a button on the second component of the game controller with the second hand and moves the second component of the game controller with the second hand and the second arm to control the video game. The first component of the game controller is separate from the second component of the game controller and can be moved independently from the second component of the game controller. The game controller sends one or more signals representative of a position of the button on the first component, of a position of the button on the second component, of a motion of the first component in 3D space and of a motion of the second component in 3D space are reported by the game controller to the computer in real time. The computer analyzes the one or more signals and controls the video game to control avatars and perform actions portrayed on the display and heard on computer speakers.

In accordance with another aspect of the present invention, the video game causes a displayed object to include one of two codes wherein a first code indicates that the displayed object can be moved with the first component of the controller and a second code indicates that the displayed object can be moved with the second component of the controller. The two codes can be, for example, different object or avatar colors.

In accordance with a further aspect of the invention, when the video game causes a displayed object to include one of two codes, the computer only allows the displayed object to be moved by either the first component or the second component of the controller in accordance with the two codes.

In accordance with another aspect of the invention, the computer monitors and stores a set of information from the first component and the second component of the controller, the set of information including: (1) activation of the button on the first component of the controller; (2) movement of the first component of the controller; (3) activation of the button on the second component of the controller; and (4) movement of the second component of the controller. The computer then controls the video game and resulting action on the display in accordance the set of information. The computer can also analyze the set of information to determine progress of the patient by assigning scores to each video game and by counting the number of repetitions performed by the first component and by the second component of the controller In accordance with yet another aspect of the invention, while holding the first and second components of the controller the patient wears wrist weights on one or both forearms. The patient may also be provided with extra oxygen through a flexible tube to the nose, so to increase oxygenation to the brain. The patient may consume food supplements designed to increase cognitive activity immediately prior to using the first and second components of the controller during video game play.

In accordance with another aspect of the invention, the computer controls the action displayed such that the action caused by the first component of the controller is the same as the action caused by the second component of the controller.

Systems that perform the methods described herein are also provided. For example, a system can also include a computer, a video game executing on the computer, a display portraying action from the video game on a display, the action being viewable and heard by the patient, a game controller having a first hand-held component with a button and a second hand-held component with a button, wherein the first component is separate from the second component and can be moved independently from the second component The game controller sends one or more signals representative of a position of the button on the first component, of a position of the button on the second component, of a motion of the first component and of a motion of the second component are reported by the game controller in real time to the computer. The computer analyzes the one or more signals and controls the video game to control action portrayed on the display such that the action caused by the first component of the controller is the same as the action caused by the second component of the controller.

The computer can also cause all other processes described herein.

The controller may be a Leap Motion controller, in which case the patient interacts with the computer through hand gestures.

It is specified that some or all of these therapeutic games may be played with wrist weights, so to increase the physical exercise component of the integrative therapy. The wrist weights are those known in the art and commerically available. It is believed that for elderly uses smaller weight values (such as 0.5 lb, 1 lb and 2 lb) are appropriate for use with the system described in this application.

Alternatively, weights can be applied to a handheld controller that is manipulated by the patient.

DESCRIPTION OF THE DRAWINGS

FIG. 3a illustrates a Razer Hydra bimanual game interface.

FIG. 3c illustrates a Velcro strip used to keep Hydra controller in the hand of a stroke patient with the forearm resting on a towel.

FIG. 4 illustrates a patient playing a game while wearing wrist weights and having an oxygen tube to the nose.

FIG. 5a illustrates an arm vertical movement baseline.

FIG. 5b illustrates an arm horizontal movement baseline.

FIG. 5c illustrates a flexion baseline for left and right index fingers.

FIG. 5d illustrates an extension baseline for left and right index fingers.

FIG. 8 illustrates a Card Island game to train short term visual memory.

FIG. 9a illustrates a card game training long term visual and auditory memory, showing Phase 1 of the game asking the patient to choose one card and remember it for later.

FIG. 9b illustrates a situation where, after a number of other games are played, the patient needs to recall the card initially selected.

DESCRIPTION

Figure 1:
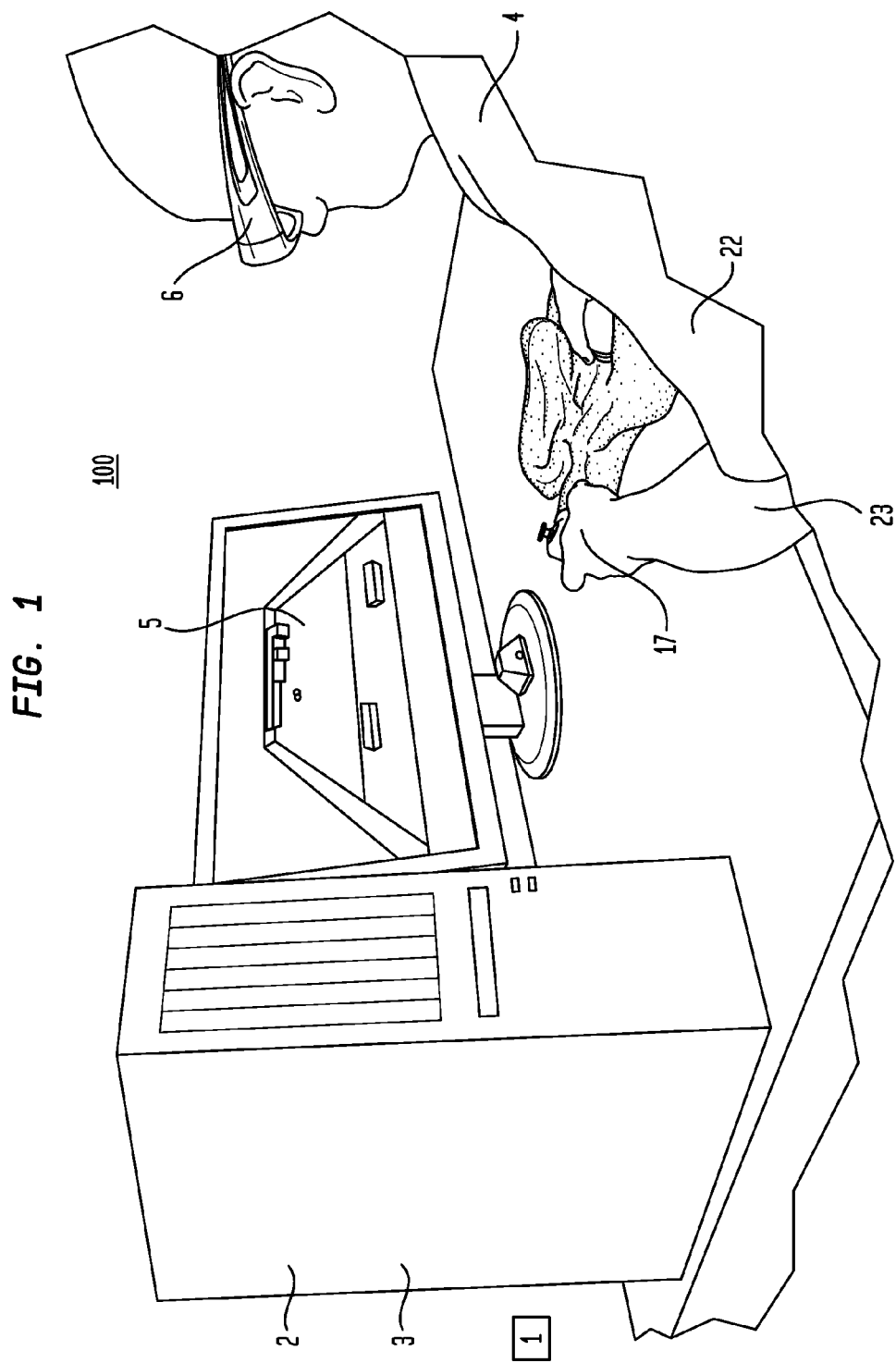
FIG. 1 illustrates a bimanual exercise system using a workstation, 3D (stereo) monitor, 3D glasses, and Hydra bimanual hand controller.

Referring to FIG. 1, the bimanual therapy system 100 consists of off-the shelf gaming hardware and a library of custom therapeutic games 1 written in Unity 3D Pro. See Reference 11. The games are rendered on a computer 2, such as those available in commerce. For example the games 1 can be rendered by an HP 2600 graphics workstation with an nVidia "Quadro 2000" graphics accelerator 3 (FIG. 1). The graphics are in 3D, so to facilitate immersion and help the patient 4 in his manual tasks. Therefore the workstation 2 is connected to an Assus VG236H 3D monitor 5, and the patient 4 wears a pair of nVidia "3D Vision" active stereo glasses 6.

Figure 2:
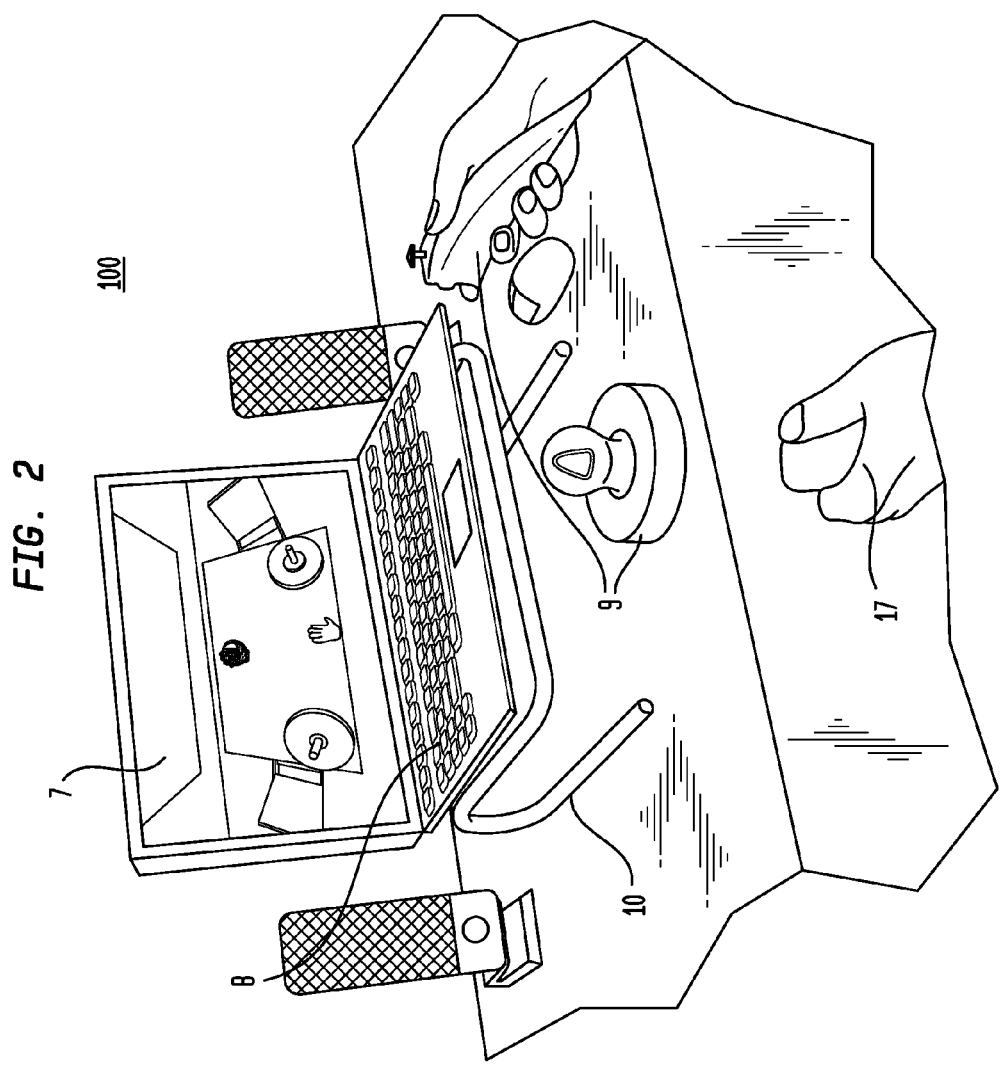
FIG. 2 illustrates a system using a gamer laptop placed on a cooling tray and the same Hydra bimanual hand controller.

Alternately the games 1 may be rendered on a 2D "gamer" laptop computer 7 such as the HP Envy with 17 in screen and nVidia GeForce GT 750M graphics accelerator 8. The same bimanual game controller 9 may be used (FIG. 2), and the laptop 7 may be placed on a cooling tray 10, such as those available commercially. It is envisioned that other computers may be used as part of the bimanual integrative therapeutic system 100.

In one embodiment, the interaction with the games is mediated by a Razer Hydra bimanual interface (Reference 12) shown in FIG. 3a. It consists of two hand-held pendants 11, each with a number of buttons 12 and a trigger 13, and a stationary source 14 connected to the workstation 2 over an USB port 15. The source 14 generates the magnetic field 16 which allows the workstation 2 to track the 3D position and orientation of each hand 17 in real time. Of the many buttons on the pendants 11, the system 100 uses an analog trigger 13 so to detect the degree of flexion/extension of the patient's index fingers 18. The pressing of these analog triggers 13 controls the closing/opening of hand avatars 19, while the position/orientation of the hand avatars 19 is determined by the position/orientation of the corresponding Hydra pendants 11. The Hydra is calibrated at the start of each session by placing the two pendants 11 next to the source 14. Its work envelope is sufficient to detect hand 17 position for a patient 4 exercising in sitting.

Weights 11A can be provided which can be slipped over the pendant 11 to increase the difficulty for the patient. The weights can be provided in a variety of forms and they can be attached to the pendants 11 (both sides) by snaps, Velcro, and other mechanical attachments.

Figure 3B:
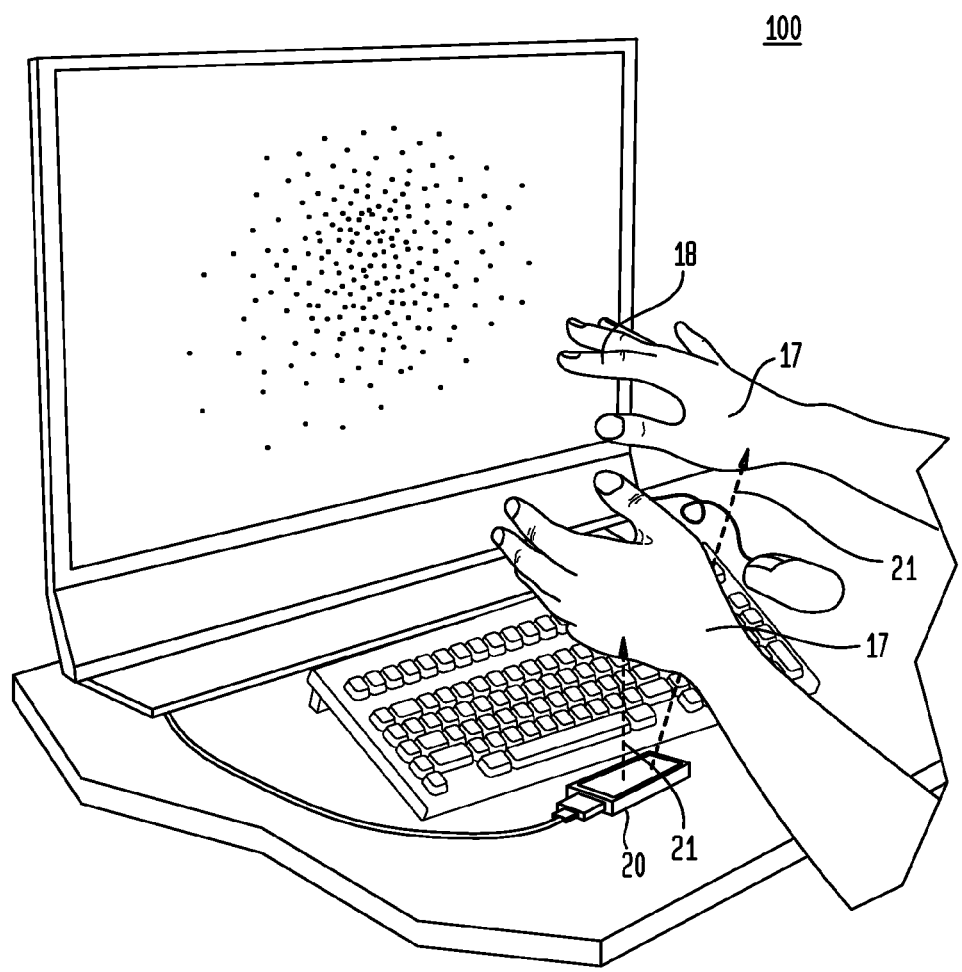
FIG. 3b illustrates a Leap Motion hand controller.

Alternately the system 100 can use a Leap Motion hand controller 20, as shown in FIG. 3b (see Reference 13). In this case the interaction is through hand 17 gestures, without the need for pendants 11. Detection of hand 17 and finger 18 movement is through infrared beams 21 emitted by the controller 20 and reflected off the hands 17 of the patient 4.

Stroke patients 4 in the acute stage (just after the neural infarct) have weak arms 22. Similarly, patients who are chronic post-stroke may have low gravity bearing capability. Some of them may also have spasticity (difficulty flexing/extending elbows 23 or fingers 18). Thus using the Hydra 9 with this population is different from use in normal play by healthy individuals. The adaptation in the present application is to place the weak arm 22 on a low-friction table 24, and use a small towel 25 under the forearm 26, so to minimize friction and facilitate forearm 26 movement. Furthermore, for spastic patients who may have difficulty holding the Hydra pendant 11 in their spastic hand 17, the solution is to use Velcro strips 27 to position the index finger 18 properly over the analog trigger 13 (see FIG. 3c).

For stronger patients 4, or those without motor impairment to their arms 22 or hands 17, it is possible to play the games 1 while wearing wrist weights 28. The amount of added physical exertion is proportional to the size of weights 28, as well as the duration of the session played while wearing the wrist weights 28. It is appreciated that elderly users 4 will feel more comfortable while wearing smaller weights 28 (0.5 lb, 1 lb, 2 lb). FIG. 4 shows a patient 4 playing a game 1 using the Hydra pendants 11, while wearing wrist weights 28. It is envisioned that the size of the wrist weights 28 may be increased over the weeks of training, with larger weights worn in later weeks.

It is further envisioned that while playing the cognitive games 1 on the system 100 which now has the commercial name of BrightBrainer™, the user 4 can also have an Oxygen tube 29 to the nose 30. The Oxygen tube 29 is of the type known in the art (transparent plastic), being small and flexible, and unencumbering to the user 4. Provision of extra Oxygen to the blood, brings extra oxygenation to the brain. This boosts the brain activity, as it facilitates energy generation and in turn helps neuronal activity. The oxygen is provided via a tank 30A.

In addition to (or instead of) wearing an Oxygen tube 29, the user 4 may choose to have food supplements 31 (such as dark chocolate, fatty fish, spinach, berries, walnuts, avocado, water intake increase, wheat germs, beats, garlic). Such food supplements 31 need to be taken some time before the play on the system 100, so to be metabolized, and facilitate increased cognitive activity.

Therapeutic Games

Several games 1 were developed to be played either uni-manually or bimanually. This gives flexibility when the therapy focus is motor re-training (using uni-manual mode), or integrative cognitive retraining (using bimanual mode). The requirement for developing a multi-game 1 therapy system 100 stems from the need to address several cognitive areas (by targeted games 1), as well as to minimize boredom by alternating games 1 during a session.

In a sequence of sessions, the first sessions can be played uni-manually so users 4 learn the games 1. In the second part they progress to using both arms 22, and finally to wearing weights 28 for increased exercising demands. It is also envisioned that in a sequence of sessions, the duration of play will be shorter in the first sessions, and progressively longer over the duration of therapy.

Baselines

Each patient 4 is different, each day. It is therefore necessary to use baselines 40 to determine the patient's 4 motor capabilities, and adapt the games 1 accordingly. The system 100 uses three baselines, two for arm range 41, 42, and one for the index finger flexion/extension 43 using the analog trigger 13 on the Hydra pendant 11. As seen in FIG. 5a, the vertical baseline 41 asks the patient 4 to draw a circle 44 on a virtual blackboard 45. The software then fits a rectangle to the "circle" 44 and this range is used to map the arm 22 limited vertical range 46 to the full vertical space on the game 1 scene. The horizontal baseline 42 (FIG. 5b) is similar, except now the patient 4 is asked to draw a circle 44 on a virtual table 47 covered by a large sheet of paper 48.

During bimanual play sessions each arm 22 performs the baselines 42, and 42 in sequence, and each arm 22 has different gains 49 mapping real movement to avatar 19 movement in the virtual scene. Thus the movement of their respective hand avatars 19 appears equal (and normal) in the virtual world, something designed to motivate the patient 4. A further reason to present exaggerated movement of the paretic arm 22 when mapped to VR is the positive role image therapy has traditionally played. In other words, the patient 4 is looking at the display 5, not at the hand 17, and believes what he or she sees on the display. This technique is similar by that developed by Burdea et al. in U.S. application Ser. No. 12/422,254 "Method for treating and exercising patients having limited range of body motion," which is incorporated herein by reference. (See Reference 14).

The third baseline 43 measures the range of movement of the index 18 of each hand 17. Unlike the range baselines 41 and 42, done in sequence, the index baseline 43 is done simultaneously for both hands 17. As seen in FIG. 5c, the patient sees two spheres 50 that move vertically between target blocks 51, in proportion with the index 18 movement on each pendant trigger 13. First the patient 4 is instructed to flex, and the two balls 50 move up a certain percentage of full range. The baseline displays the finger-specific percentage 52 of full motion. Subsequently the patient 4 is asked to extend the index 18 of each hand 17 and the balls 50 move down, again a certain percentage of full range 52 (FIG. 5d). For spastic patients 4 the paretic index 18 will have little difficulty flexing, but substantial difficulty extending. The resulting limited range for the paretic index 18, and full range of the non-paretic one are then mapped to the hand avatars 19. The two hand avatars 19 will thus show full flexing and full extension during the games 1.

Games to Train Focusing

Figure 6A:
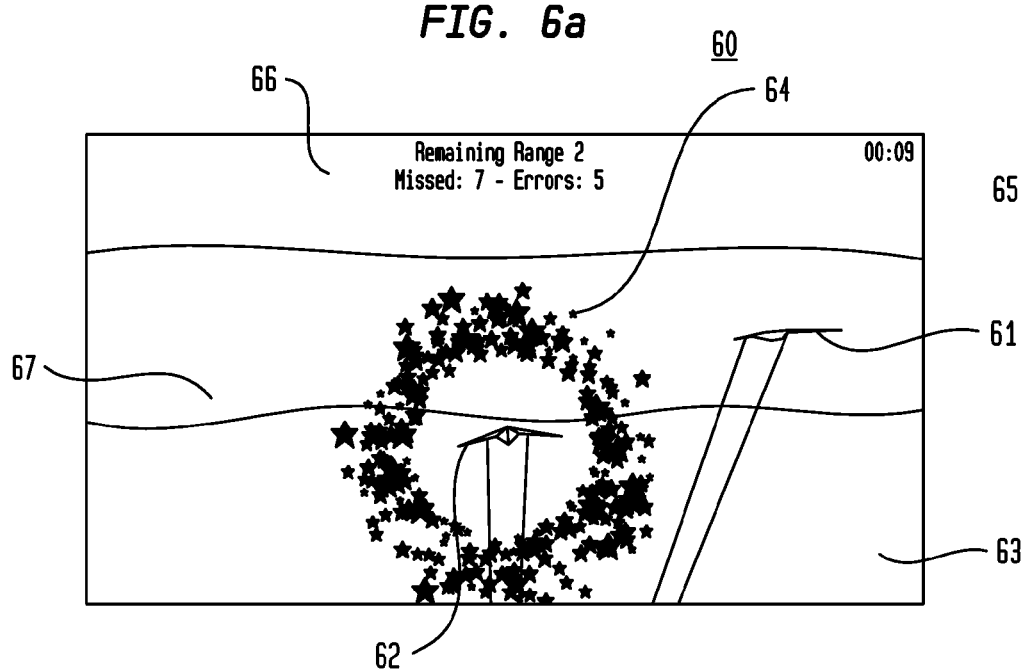
FIG. 6a illustrates a Kite game to train focusing.
Figure 6B:
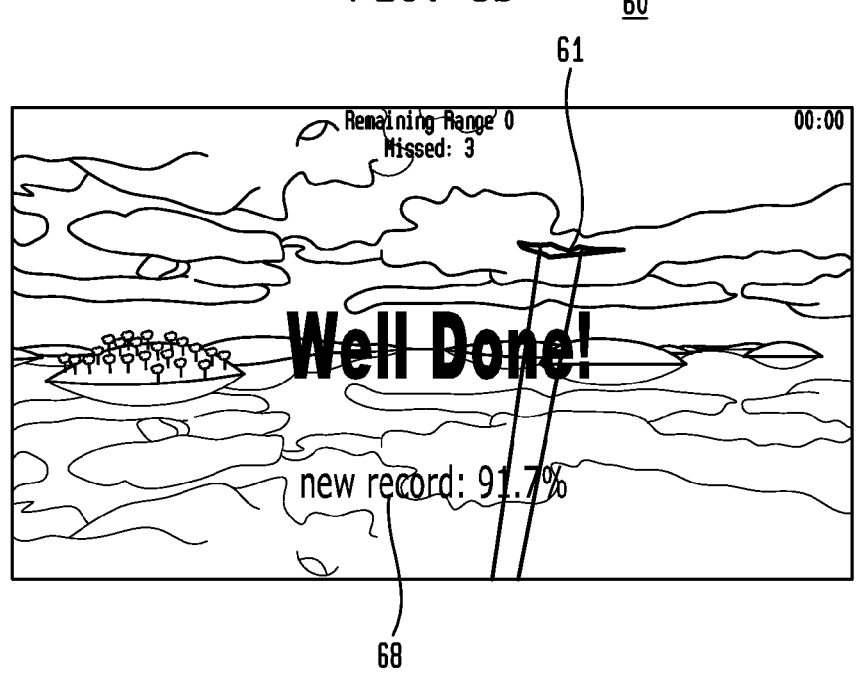
FIG. 6b illustrates a Kite game summative performance feedback.

Two games were developed to train patient's 4 ability to focus. The Kites game 60 presents two kites 61, 62 flying over water 63, while the sound of wind is heard (FIG. 6a). One kite is green, one red, and they have to be piloted through like-colored target circles 64, 65. The circles 64,65 alternate randomly in their color and their position on the screen, and the difficulty of the game 60 is modulated by the speed of the circles 64, 65, the duration of the game 60, the visibility 66 (a foggy sky gives less time to react) and the presence of air turbulence (acting as a disturbance 67). The game 60 calculates the percentage 68 of targets entered vs. those available, and displays it at the end of the game 60 as summative feedback on performance (FIG. 6b).

The Kites game 60 has a score to objectively measure patient's 4 performance:

$$\text{Success\%} * s_{kite} * f_r * \left(\frac{100}{100 - d_f}\right) * (1.2 \text{ if bimanual}) \quad (1)$$

In this game, the success rate, given by the percentage of rings caught 68, is multiplied by the redefined parameters, kite 61 speed ($s_{kite}$) and ring 64 frequency ($f_r$=number of rings per unit time), as each parameter works to increase the difficulty of the game 60. The term in parentheses considers the fog density ($d_f$), applying a higher multiplier for denser fog 66. Since all parameters other than success rate are predefined at the start of the game 60, the final score is directly proportional to the number of rings 64 hit. Finally, a 20% bonus is granted for bimanual mode so to account for increased difficulty that introduces new sources of error (hitting the ring 64 with the wrong kite 61).

Figure 7A:
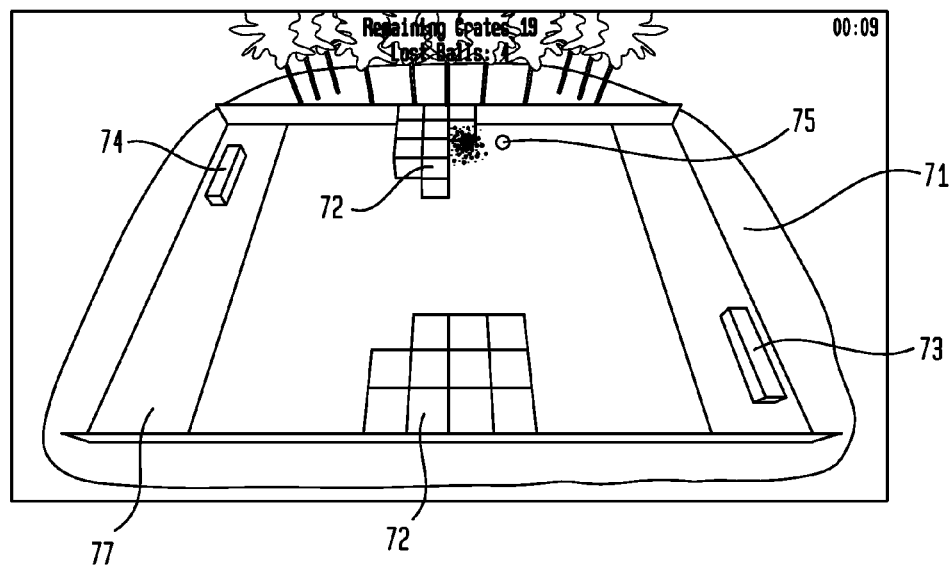
FIG. 7a illustrates a Breakout 3D game in bimanual mode which trains split attention and dual tasking in an orientation corresponding to predominantly in-out arm movement.

The Breakout 3D game 70 is a bimanual adaptation of the game developed earlier by this group for uni-manual training on the Rutgers Arm system. See Reference 15. The scene (FIG. 7a) depicts an island 71 with an array of crates 72 placed in a forest clearing. Two paddle avatars 73, 74 of different color, each controlled by one of the patient's hands 17 are located on each side of the crates 72. The patient 4 needs to bounce a ball 75 with either paddle 73, 74, so to keep it in play, and attempt to destroy all the crates 72. The ball 75 is allowed to bounce off several crates, destroying one crate 72 at each bounce. This is the preferred implementation when cognitive training is the primary focus of the game 70. If motor retraining is the primary focus of the game (such as for patients 4 post-stroke) then the ball 75 is allowed to destroy only one crate 72 after each bounce off the paddle avatar 73 or 74. This insures increase arm 22 movement demands corresponding to a given number of crates 72 to be destroyed. The sound of waves is added to help the patient 4 relax. The difficulty of the game 70 is modulated by the speed of the ball 75, the size of the paddles 73, 74, and the number of crates 72 to be destroyed in the allowed amount of time.

Figure 7B:
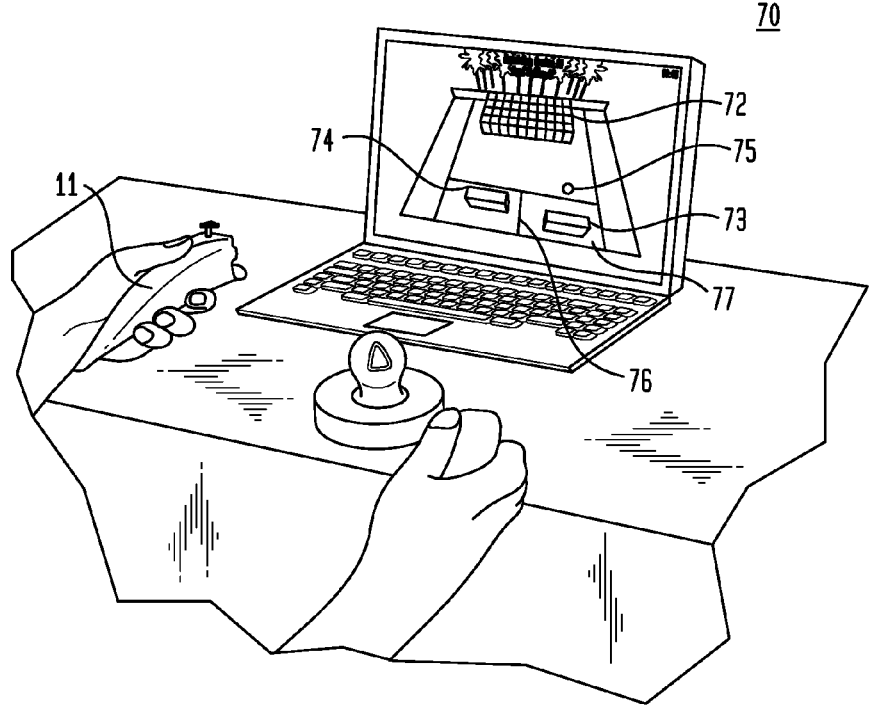
FIG. 7b illustrates Breakout 3D game in bimanual mode which trains split attention and dual tasking in an orientation corresponding to predominantly left-right arm movement.

In a different version of the Breakout 3D game 70, the paddle avatars 73,74 are close to the patient 4, and the crates 72 are further away. In this version of game 70 the predominant arm 22 movement is left-right (FIG. 7b). In this configuration a fence 76 is located at the middle of the court 77, so to prevent one paddle avatar 73, 74 from entering the other avatar's space. This features insures that the patient 4 uses both arms 22 to play the game 70. The score for Breakout 3D is given by:

$$\text{crates hit} * \left(\frac{v_{ball}}{l_{paddle}}\right) * \left(\frac{1}{\log(\text{lost balls} + 2)}\right) \quad (2)$$

The number of points awarded for each destroyed crate 72 is dependent not only on the preset parameters Ball_speed ($v_{ball}$) and Paddle_length ($l_{paddle}$), but also on the number of balls 75 lost. Since the logarithm is an increasing function, there is always a penalty for losing balls 75. Yet, as more balls 75 are lost, the penalty increases at a progressively slower rate, enabling players 4 of lesser skill to achieve better scores. The number 2 is added to prevent divide-by-zero issues (in case no balls 75 were lost).

Games to Train Memory

The first memory game is Card Island, 80 (FIG. 8), again a bimanual version of the game previously used in unimanual training on the Rutgers Arm system. The patients 4 are presented with an island 81 and an array of cards 82 placed face down on the sand 83. The array of cards 82 is divided symmetrically by a central barrier 84, such that each hand avatar 19 has to stay on its half of the island 81. When a hand avatar 19 overlaps a card 82, the patient 4 can turn it face up by squeezing the Hydra pendant trigger 13. The task is to take turns turning cards 82 face up so to find matching pairs. Since non-matching cards 82 turn face down again, the patient 4 has to remember where a given card 82 was seen before, something that trains short term visual memory. Once a card 82 had been seen, its back changes color, which is a cognitive aide to the patient 4 playing the game. The game 80 difficulty is proportional with the number of cards 82 in the array, and the allowed length of time to find all card pairs.

Card Island is scored by:

$$\left(\text{Correct matches} - \frac{\text{Errors}}{2}\right) * \left(\frac{\text{Deck Size}}{\log(\text{Playtime})}\right) \quad (3)$$

An incorrect match deducts points equal to half of a correctly matched pair. This allows players 4 a second chance to correct their mistake. If the mistake is repeated a second time, the score for eventually hitting the correct match is nullified, and deducted from the total score. Leniency is granted towards slower players 4 as exhibited by the logarithm of their playtime measured in seconds. At the same time, this leniency is also depending on the starting deck 82 size. Lastly, no performance bonus is given for bimanual play mode, as the difficulty of this game lies in the player's 4 short-term visual memory abilities.

Remember this card, 90 (FIG. 9*a*) is a game that trains long-term visual and auditory memory. The game consists of two parts 91, 92, interspaced by other games. In the first part 91 the patient 4 is presented with a number of cards 93 placed face down. Each card needs to be turned face up, at which time a sound in played associated with the image on the card. For example, if the card 93 depicts a phone booth 94, then a ring tone 95 in played. After all cards 93 had been explored, the patient 4 selects one, by flexing the hand avatar 19 over the card, and is prompted with the "Remember this card" text. After a number of other games are played, the second part of the game 92 appears, with a scene that shows the cards 93 previously explored, this time lined up face up. The patient 4 is asked to select the card he had been asked to remember before. If the attempt is unsuccessful, the "Oups, nice try!" text 95 appears (FIG. 9*b*), otherwise the patient 4 is congratulated for remembering correctly. The difficulty of the game 90 is modulated by the number of card choices 93, as well as the number of other games interposed between the two parts 91, 92 of this delayed recall game 90.

The score is:

$$\frac{50 * \text{Number of Card}}{\log(\text{Recall time} + 2)} \quad (4)$$

The score scales linearly with the number of cards 93 while being more lenient on the time taken to recall and choose the correct card. The recall time is the time taken by the patient 4 to pick their previously selected card among those shown, measured in seconds. For any given number of cards 93 in this formula, a player 4 who takes less time to choose the correct card will always receive a higher score than a slower player. However, the slower players will not see a larger gap in scores, regardless of how long they take to remember the original card. Again, 2 (measured in seconds) is added to the recall time in order to prevent divide-by-zero errors.

Game to Train Executive Function

Towers of Hanoi 3D game, 110 is similar to the version of the game being played with a mouse online. The patient 4 has to restack a pile of disks 111 of different diameters, from one pole 112 to another pole 113, using a third pole 114 as way-point. The game 110 trains decision making/problem solving by setting the condition that no disk 111 can be placed on top of a smaller diameter one.

Figure 10:
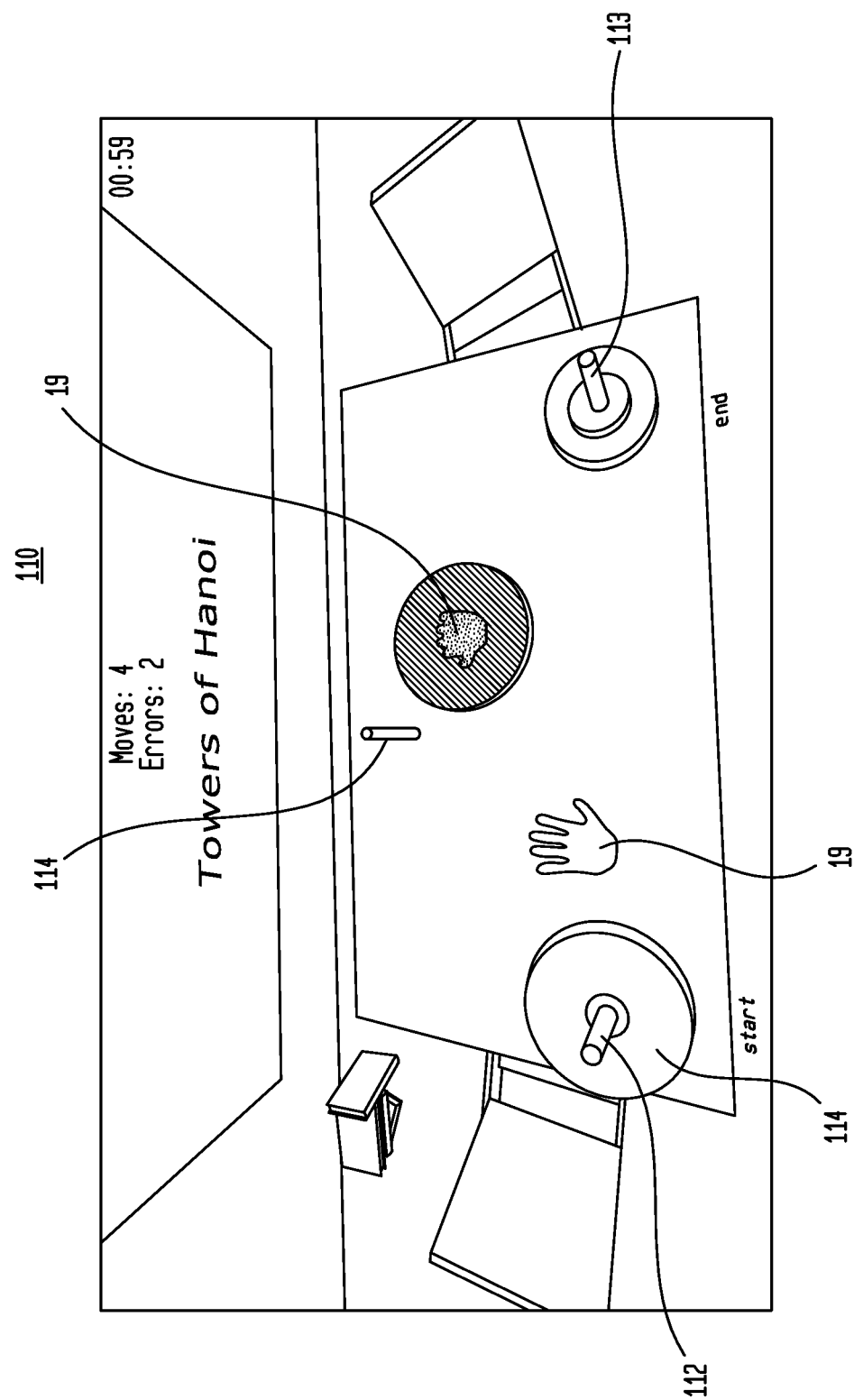
FIG. 10 illustrates the use of the Towers of Hanoi 3D game to train executive function wherein two hand avatars are allowed to only manipulate like-colored disks.

In the version of the game 110 for bimanual therapy, the scene shows two hand avatars 19, one green and one red and similarly colored red and green disks 111 (FIG. 10). Each hand avatar 19 is allowed to manipulate only disks 111 of similar color. The game 110 chooses randomly the green or the red color for the smallest disk and allocates the other color to the other disks. In this configuration, both hands 17 are doing approximately the same number of moves. The difficulty of the game 110 depends on the number of disks 111 (2—easy, 3—medium, 4—difficult). The number of moves in the game 110 is counted and compared to the ideal (smallest) number of moves to complete the task. Thus cognitively, achieving an economical (minimal) number of moves to solve the problem is indicative of good problem solving skills.

The score is:

$$\frac{150 * \text{disks} * (1.2 \text{ if bimanual})}{\log(\text{moves} - \text{pow}(2, \text{disks}) + 1) * \log(\text{Playtime})} \quad (5)$$

If a patient 4 was unable to complete the game 110, we assign a flat score of 100, so to maintain patient 4 motivation. In this game, each disk 111 is worth 150 points, with 20% increase in bimanual play mode to account for the increased difficulty and newly introduced sources of error. This number is countered by a product of logarithms (for leniency): the first compares the number of moves made by the patient 4 against the optimal solution, and the second factors in the time taken to solve the task.

Dual Tasking and Therapy Gradation

As stated before, dual tasking is typically problematic with older populations (whether stroke survivors or not). Thus some of the games have embedded dual-tasking features, notably Breakout 3D 70. When the dual tasking parameter is set, the paddle avatar 73, 74 characteristics depend on whether the trigger 13 is squeezed during movement or not. When a momentary squeeze is required, the patient 4 has to squeeze the trigger 13 at the moment of bounce, lest the ball 75 passes through the paddle 73, or 74 and is lost. When a sustained grasp is required, the movement of the paddle 73, 74 is decoupled from that of the pendant 11 when the trigger 13 is not squeezed. Thus the patient 4 has to remember to keep squeezing to move the paddle 73, 74 to bounce the ball 75. Recognizing that sustained squeezing may be fatiguing and may induce discomfort for some patients 4, the game 70 sets a threshold as a % of range when classifying an index 18 flexion as a squeeze. This threshold is based on the finger 18 flexion baseline 40 previously described.

Naturally, the introduction of the squeezing requirement further increases game 70 difficulty. Thus the weeks of therapy are gradated in terms of session duration and game difficulty. The approach in this application is to begin with shorter sessions of 30 minutes in week 1, progress to 40 minutes in week 2 and 50 minutes for the remaining weeks. The games in week 1 are uni-manual and played with the non-paretic arm 22, so to familiarize the patient 4 with the system 100 and its games 1. Gradually the games 1 difficulty is increased, switching to bimanual mode in week 2 or later, and in the last 3 weeks the dual tasking condition is introduced. The aim is to always challenge the patient 4, offer variety, but make games 1 winnable, so to keep motivation high.

Arm 22 and Index 18 Repetitions 120

It is Known in the Art that the Amount of Movement Repetitions 120 within a Task is Crucial to induce brain plasticity. Within the system 100 described here the tasks are dictated by the different games 1, and the system 100 measures the number of repetitions 120 during play, The number of repetitions 120 is arm specific, as well as index finger 18 specific (right, left), and is summed for the session. The amount of repetitions 120 is an indication of the intensity of play, and a useful tool for the therapist.

Figure 11:
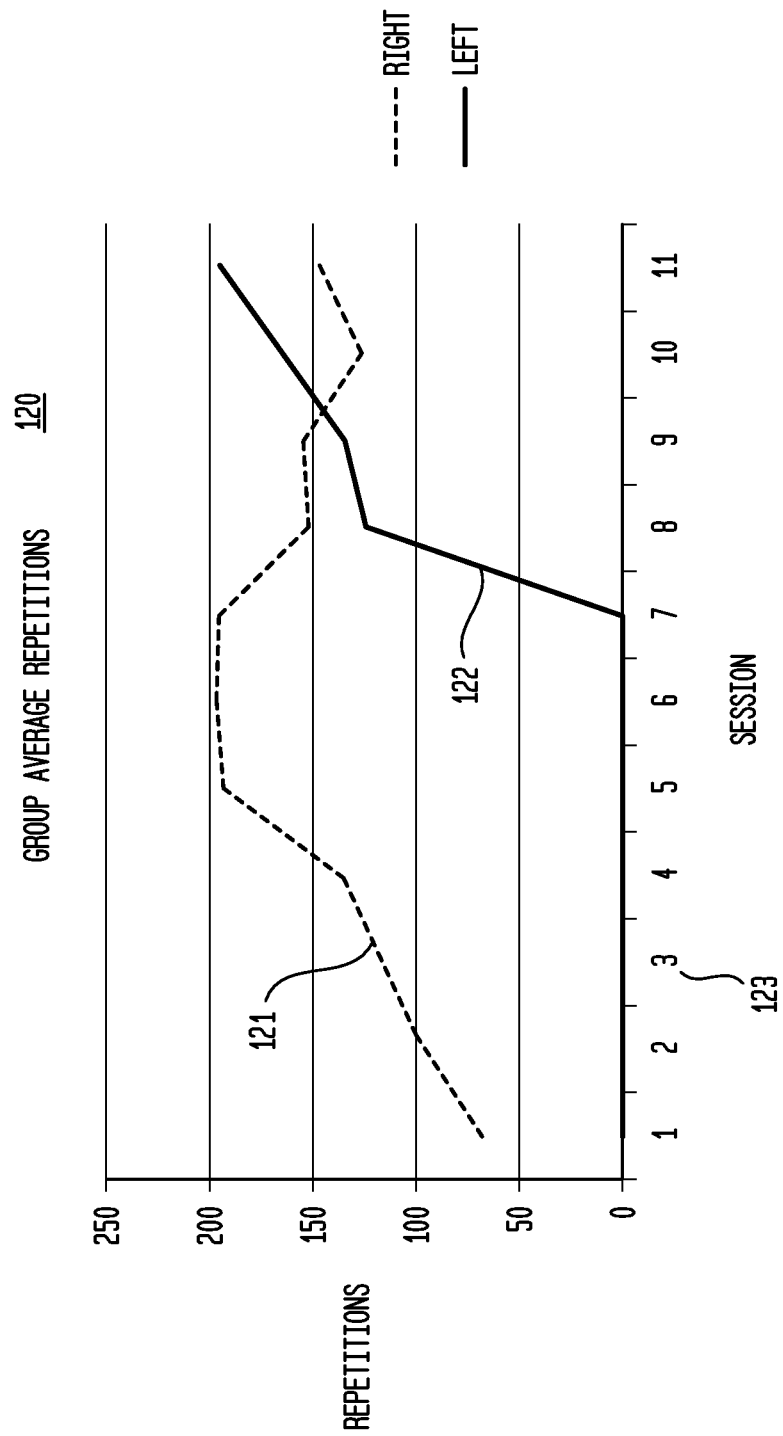
FIG. 11 shows a graph depicting average right and left arm repetitions during group training over a sequence of sessions.

In group therapy the repetitions 120 may be averaged over the group of patients 4 for a given session. FIG. 11 depicts a graph showing the left and right arm 22 number of repetitions 121, 122 over a sequence of sessions 123. It can be seen that over the first 7 sessions the right arm number of repetitions 121 grows, while the left arm 22 is motionless. This is due to the fact that during these 7 sessions the games 1 were played in uni-manual mode, and thus only the right arm was used. The reason the number of repetitions 121 increases for right arm 22 is the increased session duration, implying more games played. Once the games 1 started being played with both arms 22, it can be seen that the left arm 22 has a steep increase in its number of movement repetitions 122, while the right arm number of repetitions 121 is somewhat reduced. Eventually both arms share about equally in the game play.

Discussion

A pilot feasibility study took place with two elderly participants who were in the chronic phase of stroke and had arm/hand spasticity (See Reference 16). A short video can be submitted to show one of participants during therapy.

The feasibility study aim was to determine technology acceptance as well as any clinical benefits in the cognitive and emotive domain. These were measured by a blinded neuro-psychologist consultant using standardized tests. Results showed excellent technology acceptance and benefits to the two patients 4 in various cognitive domains. One patient had reduced depression following the therapy.

Subsequently a larger study with 10 elderly nursing home residents took place in summer 2013. See reference 17. Eight of the patients 4 had dementia and one had severe traumatic brain injury. They played the games described above and three other games we developed. The new games were: Pick-and-Place bimanual 130, Xylophone bimanual 140, and Musical Drums 150, bimanual.

Figure 12:
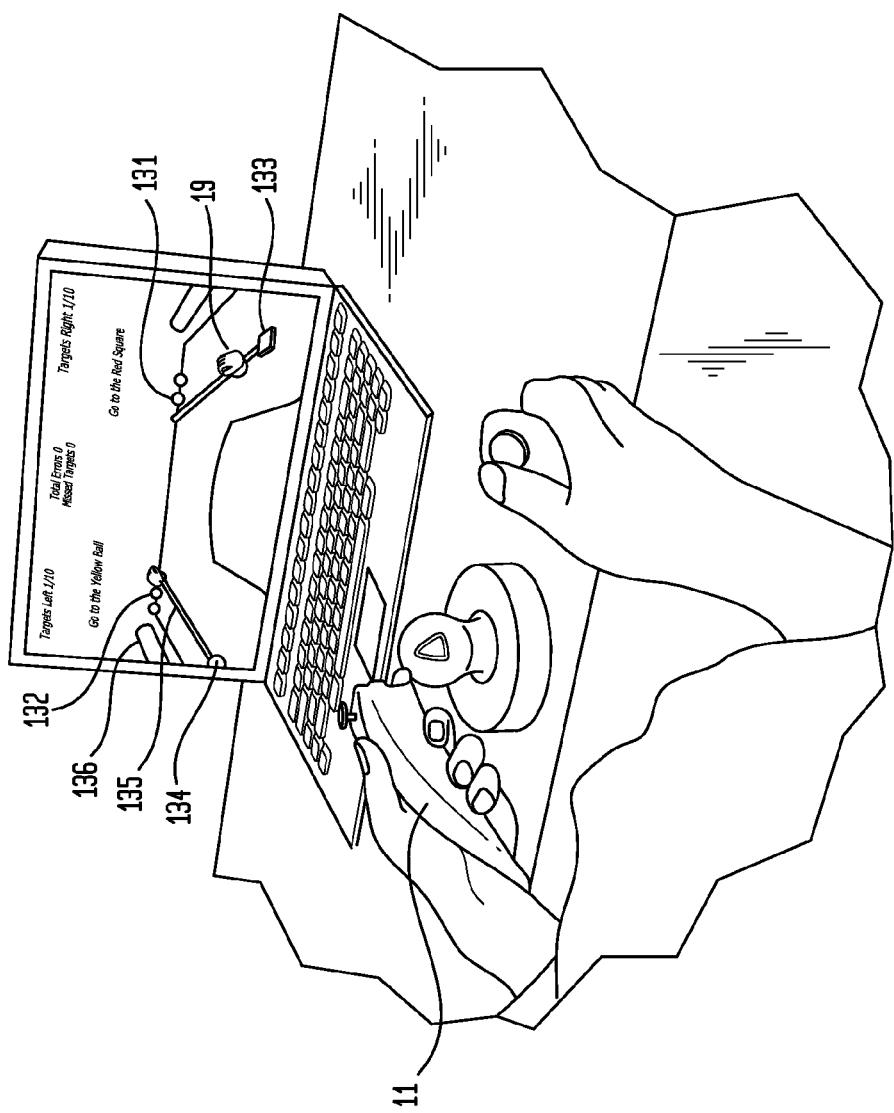
FIG. 12 illustrates a Pick-and-Place bimanual game.

The Pick-and-Place game 130 bimanual (FIG. 12) shows two hand avatars 19 that need to pick a ball 136 each from three possible choices 131, 132 and move them to target areas 133, 134 following prescribed (ideal) paths 135. Each time a ball 136 is correctly moved to a target 133, 134, a different sound is played. The patient 4 has a choice of moving one ball at a time or of moving both arms 22 at the same time (a more difficult task). The game 130 difficulty depends on the number of required repetitions, and errors are counted whenever the wrong ball is picked up. The Pick-and-Place game trains hand-eye coordination and dual tasking may be introduced by requiring the patient to squeeze the Hydra trigger 13 to keep the ball 136 grasped by avatar 19.

Figure 13:
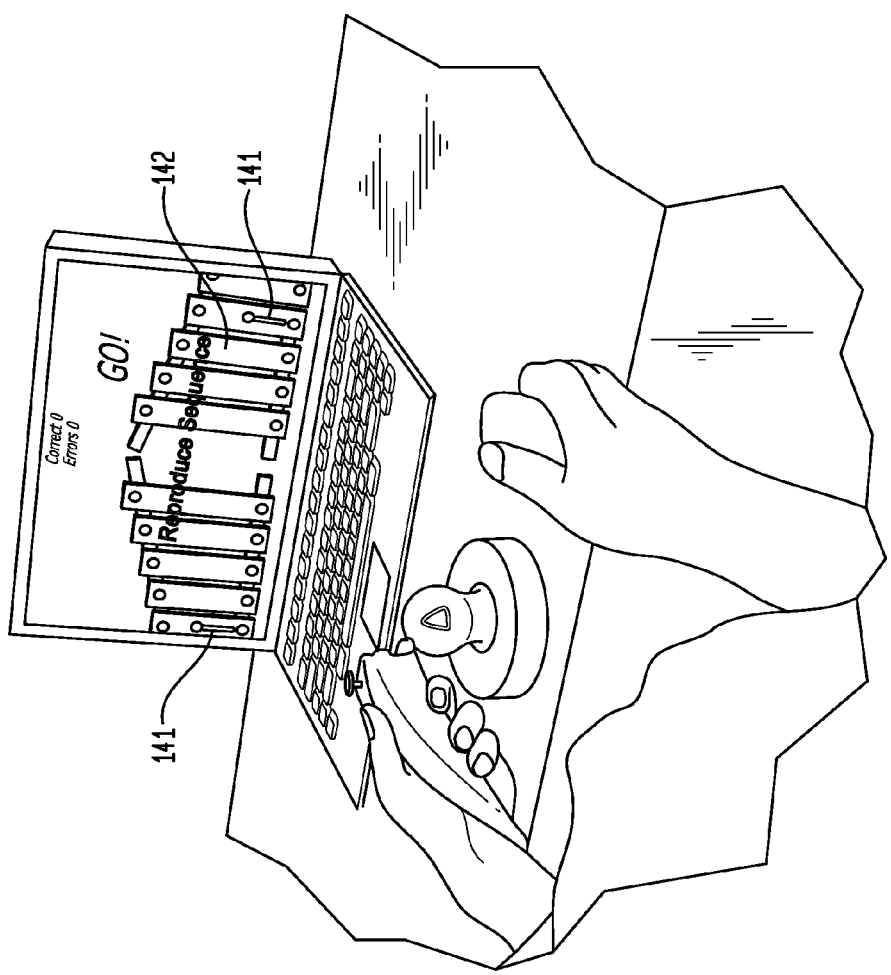
FIG. 13 illustrates a Xylophone bimanual game.

In the Xylophone game 140 (FIG. 13) the patient 4 controls two hammer avatars 141, and needs to hit keys 142 to create a sound (play a note). The patient 4 is tasked with reproducing sequences of notes by playing the instrument keys 142 in the correct order. The difficulty of the game depends on the length of note sequences to be reproduced, as well as the total amount of time available to complete a series of note sequences.

Figure 14:
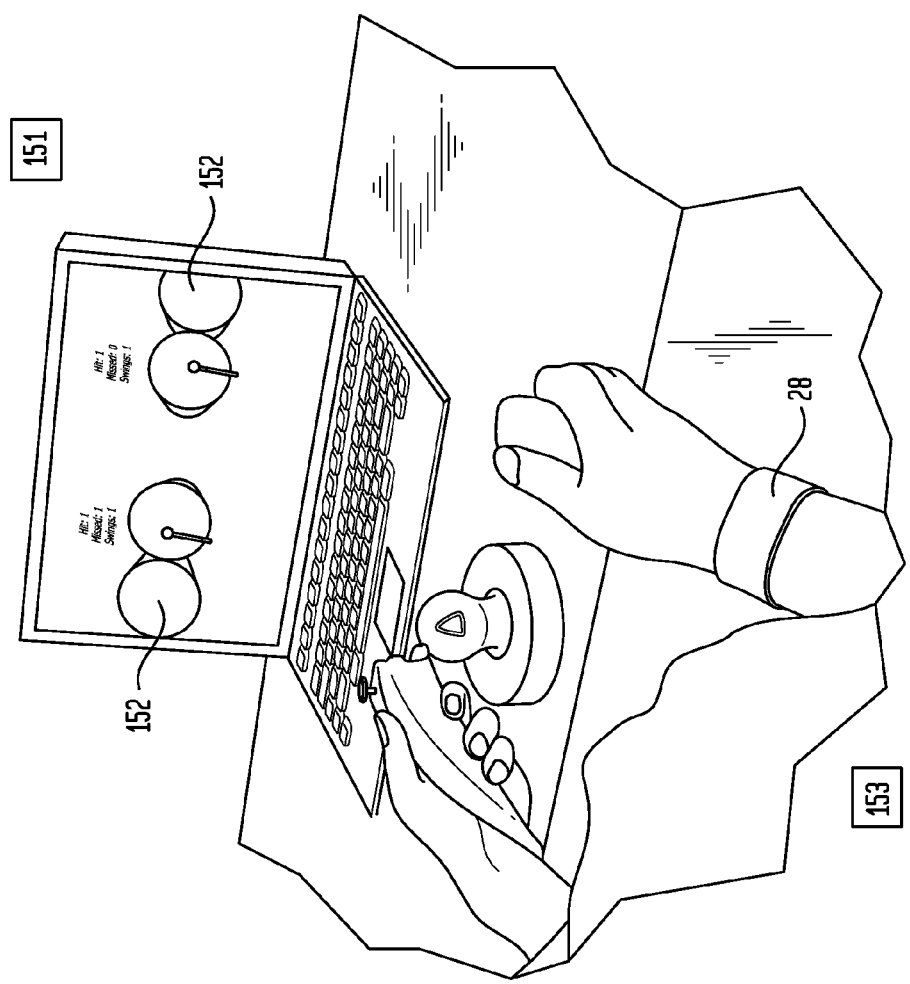
FIG. 14 illustrates a Musical Drums bimanual game.

Another game is Musical Drums 150 (FIG. 14) where the patient 4 needs to hit notes 151 scrolling on the screen when they overlap a drum 152 to get points. The difficulty of the game 150 increases with the tempo of the song 153 being played, corresponding to faster scrolling of the notes 151 across the screen. Further increase in difficulty occurs when notes scroll across more drums 152.

Patients had to play the games two times per week for 8 weeks. To measure clinical benefit, tests were done by a blinded neuropsychologist before and after the 8 weeks of therapy. These tests showed statistically significant group improvement in decision making capacity, and borderline significant reduction in depression.

In summary, one aspect of the present invention is to provide a method of providing therapy to a patient having a first arm, a first hand, a second arm and a second hand. The method includes executing a video game on a computer and portraying action from the video game on a display, the action being viewable by the patient; the patient holding a first component of a game controller in the first hand and manipulating an interface on the first component of the game controller with the first hand and moving the first component of the game controller with the first hand and the first arm to control the video game; the patient holding a second component of a game controller in the second hand and manipulating an interface on the second component of the game controller with the second hand and moving the second component of the game controller with the second hand and the second arm to control the video game. The first component of the game controller is separate from the second component of the game controller and can be moved independently from the second component of the game controller. The game controller sends one or more signals representative of a position of the interface on the first component, of a position of the interface on the second component, of a motion of the first component and of a motion of the second component are reported by the game controller to the computer; and the computer analyzes the one or more signals and controlling the video game to control action portrayed on the display.

The video game can also control the computer to cause a displayed object to include one of two codes wherein a first code indicates that the displayed object can be moved with the first component of the controller and a second code indicates that the displayed object can be moved with the second component of the controller. Preferably, the two codes are different colors.

While the game is played the computer monitors and stores a set of information from the first component and the second component of the controller. The set of information includes: activation of the interface (button and trigger) on the first component of the controller; movement of the first component of the controller; activation of the interface on the second component of the controller; and movement of the second component of the controller.

The computer controls the video game and resulting action on the display in accordance the set of information. The computer also analyzes the set of information to determine progress of the patient. In one embodiment of the present invention, the computer controls the action displayed such that the action caused by the first component of the controller is the same as the action caused by the second component of the controller even if one of the arms does not perform as well. As explained before, extra oxygen can be fed to the patient from an oxygen tank while the patient manipulates the first component and the second component. Also as explained before the patient can wear wrist weights on the first arm, on the second arm or on both arms while the patient manipulates the first component and the second component. Alternatively, weights can be added to either the first component of the game controller, to the second component of the game controller or to both. The handheld components can be modified to have the weights attached to them.

In accordance with an aspect of the present invention, the computer controls a videogame avatar object in response to activation of the interface (button and/or trigger) on each of the handheld components of the controller. The avatar object can be controlled by movement of each handheld component of the controller. Alternatively, one avatar object can be controlled by the movement of the first (say the left) handheld component while another avatar object can be controlled by the movement of the second (say the right) handheld component. Thus, a computer can control a videogame avatar object to respond to movement of the first component of the controller if the button or the trigger on the first component are pressed and the computer controls another video game avatar object to respond to movement of the second component of the controller if the button or the trigger on the second component are pressed.

A system of providing therapy to a patient having a first arm, a first hand, a second arm and a second hand, is also provided as explained above.

The following is a list of references referred to herein, each of which is incorporated by reference:

Reference No. 1—Roger V L, Go A S, Lloyd-Jones D M, Benjamin E J, Berry J D, Borden W B, et al. Heart disease and stroke statistics-2012 update: a report from the American Heart Association. Circulation. 2012; 125(1): e2-220.

Reference No. 2—C. Y. Wu, L. L. Chuang, K. C. Lin, H. C. Chen and P. K. Tsay, Randomized trial of distributed constraint-induced therapy versus bilateral arm training for the rehabilitation of upper-limb motor control and function after stroke. *Neurorehab Neural Re*, Vol. 25, 2, pp. 130-139, 2011.

Reference No. 3—J. H. Cauraugh, N. Lodha, S. K. Naik and J. J. Summers, Bilateral movement training and stroke motor recovery progress: a structured review and meta-analysis. *Hum Movement Sci*, Vol 29, 5, pp. 853-870, 2010.

Reference No. 4—C. Ausenda and M. Carnovali, Transfer of motor skill learning from the healthy hand to the paretic hand in stroke patients: a randomized controlled trial. *Eur J Phys Rehabil Med*, Vol. 47, 3, pp. 417-425, 2011.

Reference No. 5—G. Burdea, Virtual rehabilitation-benefits and challenges. *J Meth Inform Med*, pp. 519-523, 2003.

Reference No. 6—C. Brooks, B. Gabella, R. Hoffman, D. Sosin, and G. Whiteneck, Traumatic brain injury: designing and implementing a population-based follow-up system. *Arch Phys Med Rehab*, 78, pp. S26-S30, 1997.

Reference No. 7—M. Wang, N. J. Gamo, Y. Yang, L. E. Jin, X. J. Wang, et al., Neuronal basis of age-related working memory decline, *Nature*, Vol 476, pp. 210-213, July, 2011.

Reference No. 8—K. Lin, Y. Chen, C. Chen, C. Y. Wu and Y. F. Chang, The effects of bilateral arm training on motor control and functional performance in chronic stroke: a randomized controlled study, *Neurorehab Neural Re*, Vol 24; pp. 42-51, 2010.

Reference No. 9—P. W. Duncan, M. Probst, and S. G. Nelson, Reliability of the Fugl-Meyer assessment of sensorimotor recovery following cerebrovascular accident. *Phys Ther*, Vol 63, pp. 1606-1610, 1983.

Reference No. 10—G. Optale, C. Urgesi, V. Busato, S. Marin, L. Piron et al., Controlling memory impairment in elderly adults using virtual reality memory training: a randomized controlled pilot study. *Neurorehab Neural Re*, Vol 24, 4, pp. 348-357, 2010.

Reference No. 11—Unity Technologies, Reference Manual. San Francisco, Calif., 2010.

Reference No. 12—Sixense Entertainment, Razer Hydra Master Guide, 11 pp., 2011.

Reference No. 13—CNet Leap Motion controller review: Virtual reality for your hands. Jul. 22, 2013. http://reviews.cnet.com/input-devices/leap-motion-controller/4505-3133_7-35823002.html.

Reference No. 14—G. Burdea and M. Golomb, U.S. patent application Ser. No. 12/422,254 "Method for treating and exercising patients having limited range of body motion, Apr. 11, 2009.

Reference No. 15—G. Burdea, D. Cioi, J. Martin, D. Fensterheim and M. Holenski, The Rutgers Arm II rehabilitation system—a feasibility study, *IEEE Trans Neural Sys Rehab Eng*, Vol 18, 5, pp. 505-514, 2010.

Reference No. 16—G. Burdea, C. Defais, K. Wong, J. Bartos and J. Hundal, "Feasibility study of a new game-based bimanual integrative therapy," Proceedings $10^{th}$ Int. Conference on Virtual Rehabilitation, Philadelphia, Pa., August 2013, pp. 101-108.

Reference No. 17—G. Burdea, K. Polistico, A. Krishnamoorthy, J. Hundal, F. Damiani, S. Pollack, "A Feasibility study of BrightBrainer™ cognitive therapy for elderly nursing home residents with dementia," Disability and Rehabilitation—Assistive Technology.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims and in view of the specification.

The invention claimed is:

1. A method of providing therapy to a patient having a first arm, a first hand, a second arm and a second hand, comprising:

executing a video game on a computer comprising a display and portraying action from the video game on the display, the action being viewable by the patient;

the patient holding a first component of a game controller in the first hand, manipulating an interface on the first component of the game controller with the first hand, and moving the first component of the game controller with the first hand and the first arm to control the video game;

the patient holding a second component of a game controller in the second hand, manipulating an interface on the second component of the game controller with the second hand, and moving the second component of the game controller with the second hand and the second arm to control the video game;

wherein the first component of the game controller is separate from the second component of the game controller and can be moved independently from the second component of the game controller;

the game controller sending one or more signals representative of a position of the interface on the first component, of a position of the interface on the second component, of a motion of the first component, and of a motion of the second component, wherein the signals are reported by the game controller to the computer; and the computer analyzing the one or more signals and controlling the video game to control action portrayed on the display, wherein the action portrayed on the display comprises an avatar representative of the patient's first hand, holding the first component of the game controller, and an avatar representative of the patient's second hand, holding the second component of the game controller, wherein the patient's first arm has a more limited range of movement than the patient's second arm, wherein vertical and horizontal movement of the respective hand avatars on the display is adjusted according to a baseline of the patient's motor capabilities such that a range of movement of the patient's first arm is exaggerated to be substantially equal to a range of movement of the patient's second arm.

2. The method of claim 1, comprising the video game causing a displayed object to include one of two codes wherein a first code indicates that the displayed object can be moved with the first component of the controller and a second code indicates that the displayed object can be moved with the second component of the controller.

3. The method of claim 2 wherein the two codes are different colors.

4. The method of claim 1, comprising the video game causing a displayed object to include one of two codes wherein the computer only allows the displayed to be moved by either the first component or the second component of the controller in accordance with the two codes.

5. The method of claim 1, comprising the video game causing a displayed object to include a first code or a second code and the computer only allowing displayed objects that include the first code to be moved by the first component of the controller and the computer only allowing displayed objects that include the second code to be moved by the second component of the controller.

6. The method of claim 1, comprising the computer monitoring and storing a set of information from the first component and the second component of the controller, the set of information including:
   activation of the interface on the first component of the controller;
   movement of the first component of the controller;
   activation of the interface on the second component of the controller;
   movement of the second component of the controller; and
   total number of repetitions of movement of the first arm over a video game and over a session of therapy and total number of repetitions of the second arm over a video game and over a session of therapy.

7. The method of claim 6, wherein the computer controls the video game and resulting action on the display in accordance with the set of information.

8. The method of claim 6, wherein the computer analyzes the set of information to determine progress of the patient.

9. The method of claim 1, wherein extra oxygen to help neural activity by improving brain oxygenation is fed to the patient from an oxygen tank while the patient manipulates the first component and the second component.

10. The method of claim 1, wherein cognition enhancing food supplements are fed to the patient a short time before commencing a therapy session.

11. The method of claim 10, wherein the cognition enhancing food supplements comprise one or more of dark chocolate, fatty fish, spinach, berries, walnuts, avocado, wheat germ, beets, or garlic.

12. The method of claim 1, wherein the patient wears wrist weights on the first arm, on the second arm or on both arms while the patient manipulates the first component and the second component.

13. The method of claim 1, wherein weights are added to either the first component of the game controller, to the second component of the game controller or to both.

14. The method of claim 1 wherein the interface on the first component and the interface on the second component includes a button and a trigger and the computer controls a videogame avatar object to respond to movement of the first component of the controller if the button or the trigger on the first component are pressed and the computer controls another video game avatar object to respond to movement of the second component of the controller if the button or the trigger on the second component are pressed.

15. A system of providing therapy to a patient having a first arm, a first hand, a second arm and a second hand, comprising:
   a computer;
   a video game executing on the computer;
   a display portraying action from the video game, the action being viewable by the patient;
   a game controller having a first hand-held component with a button and a trigger and a second hand-held component with a button and a trigger, wherein the first component is separate from the second component and can be moved independently from the second component;
   the game controller sending one or more signals representative of a position of the button and the trigger on the first component, of a position of the button and a trigger on the second component, of a motion of the first component, and of a motion of the second component wherein the motions are reported by the game controller to the computer; and
   the computer analyzing the one or more signals and controlling the video game to control action portrayed on the display,
   wherein the action portrayed on the display comprises an avatar representative of the patient's first hand, holding the first component of the game controller, and an avatar representative of the patient's second hand, holding the second component of the game controller,
   wherein the patient's first arm has a more limited range of movement than the patient's second arm,
   wherein vertical and horizontal movement of the respective hand avatars on the display is adjusted according to a baseline of the patient's motor capabilities such that a range of movement of the patient's first arm is exaggerated to be substantially equal to a range of movement of the patient's second arm.

16. The system of claim 15, wherein the video game causes a displayed object to include one of two codes wherein a first code indicates that the displayed object can be moved with the first component of the controller and a second code indicates that the displayed object can be moved with the second component of the controller.

17. The system of claim 15, wherein the video game causes a displayed object to include one of two codes wherein the computer only allows the displayed to be moved by either the first component or the second component of the controller in accordance with the two codes.

18. The system of claim 15, wherein the video game causes a displayed object to include a first code or a second code and the computer only allowing displayed objects that include the first code to be moved by the first component of the controller and the computer only allowing displayed objects that include the second code to be moved by the second component of the controller.

19. The system of claim 15, wherein the computer monitors and stores a set of information from the first component and the second component of the controller derived from successive uses of the system, the set of information including:
   activation of the interface on the first component of the controller;
   movement of the first component of the controller;
   activation of the interface on the second component of the controller;

movement of the second component of the controller; and
total number of repetitions of movement of the first arm over a video game and over a session of therapy, and total number of repetitions of the second arm over a video game and over a session of therapy.

20. The system of claim 19, wherein the computer controls the video game and resulting action on the display in accordance the set of information and the computer analyzes the set of information to determine progress of the patient, wherein the computer controls a videogame avatar object to respond to first component movement if the interface on the first component trigger is manipulated and to respond to second component movement if the interface on the second component is manipulated.

* * * * *